US010564150B2

(12) United States Patent
Boyle et al.

(10) Patent No.: US 10,564,150 B2
(45) Date of Patent: Feb. 18, 2020

(54) CELL MEDIATED IMMUNE RESPONSE ASSAY

(71) Applicant: Cellestis Limited, Chadstone, Victoria (AU)

(72) Inventors: Jeff Boyle, Pearcedale (AU); Ashley Knights, Chadstone (AU); Carmen Munian, Chadstone (AU)

(73) Assignee: Cellestis Limited, Chadstone, Victoria (AU)

( * ) Notice: Subject to any disclaimer, the term of this patent is extended or adjusted under 35 U.S.C. 154(b) by 6 days.

(21) Appl. No.: 14/758,189

(22) PCT Filed: Dec. 20, 2013

(86) PCT No.: PCT/AU2013/001509
§ 371 (c)(1),
(2) Date: Jun. 26, 2015

(87) PCT Pub. No.: WO2014/100853
PCT Pub. Date: Jul. 3, 2014

(65) Prior Publication Data
US 2015/0330972 A1    Nov. 19, 2015

Related U.S. Application Data

(60) Provisional application No. 61/746,965, filed on Dec. 28, 2012.

(30) Foreign Application Priority Data

May 10, 2013 (EP) ................................. 13167355

(51) Int. Cl.
*C12N 5/0783* (2010.01)
*G01N 33/50* (2006.01)
*A61K 39/245* (2006.01)
*A61K 39/12* (2006.01)
*C12N 5/078* (2010.01)

(52) U.S. Cl.
CPC ......... *G01N 33/5091* (2013.01); *A61K 39/12* (2013.01); *A61K 39/245* (2013.01); *G01N 33/5047* (2013.01); *C12N 5/0634* (2013.01); *C12N 5/0638* (2013.01); *C12N 2500/34* (2013.01); *C12N 2710/16122* (2013.01); *C12N 2710/16134* (2013.01); *C12N 2710/16222* (2013.01); *G01N 2333/57* (2013.01)

(58) Field of Classification Search
CPC .......................... C12N 5/0634; C12N 2500/34
See application file for complete search history.

(56) References Cited

U.S. PATENT DOCUMENTS

| 4,016,043 A | 4/1977 | Schuurs et al. |
| 4,018,653 A | 4/1977 | Mennen |
| 4,424,279 A | 1/1984 | Bohn et al. |
| 4,891,319 A | 1/1990 | Roser |
| 6,617,170 B2 | 9/2003 | Augello et al. |
| 7,270,953 B2 | 9/2007 | Holländer et al. |
| 9,983,207 B2 * | 5/2018 | Boyle .............. G01N 33/56966 |
| 2005/0014205 A1 * | 1/2005 | Rothel ............... G01N 33/5047 435/7.21 |
| 2009/0098172 A1 * | 4/2009 | Ikemoto ................... A61K 8/06 424/401 |
| 2014/0220601 A1 * | 8/2014 | Boyle .............. G01N 33/56966 435/7.92 |

FOREIGN PATENT DOCUMENTS

| CN | 1262131 A | 8/2000 | |
| EP | 1 312 670 A1 | 5/2003 | |
| EP | 1 529 536 A1 | 5/2005 | |
| WO | 98/58259 A1 | 12/1998 | |
| WO | 00/56365 A1 | 9/2000 | |
| WO | 2004/042396 A1 | 5/2004 | |
| WO | WO-2004042396 A1 * | 5/2004 | ......... G01N 33/5047 |
| WO | 2005/118629 A1 | 12/2005 | |
| WO | 2007/038926 A1 | 4/2007 | |
| WO | 2008/113119 A1 | 9/2008 | |
| WO | 2010/009494 A1 | 1/2010 | |
| WO | 2011/075773 A1 | 6/2011 | |
| WO | WO-2011131720 A1 * | 10/2011 | ........... A61K 9/0019 |
| WO | 2011/146968 A1 | 12/2011 | |
| WO | 2012/177970 A1 | 12/2012 | |

OTHER PUBLICATIONS

Gilleron et al. (J. Exp. Med. Mar. 1, 2004; 199 (5): 649-659).*
Lee et al. (Biomacromolecules. Aug. 12, 2013; 14 (8): 2561-9).*
Mancini et al. (J. Am. Chem. Soc. 2012; 134 (20): 8474-9).*
Teramoto et al. (Molecules. Aug. 21, 2008; 13 (8): 1773-816).*
Jiang et al. (BMC Immunol. May 28, 2009; 10: 31).*
Lalvani et al. (Enferm. Infecc. Microbiol. Clin. Apr. 2010; 28 (4): 245-52).*
Rombach et al. (BioTechniques. Sep. 2014; 57 (3): 151-5).*
Bowen et al. (Biochemia Medica 2014; 24 (1): 31-44).*
ten Hacken et al. (Eur. Respir J. Feb. 1998; 11 (2): 312-6).*
Kleiner et al. (Mediators Inflamm. 2013; 2013: 434010; pp. 1-6).*
Schoenborn et al. (Adv. Immunol. 2007; 96: 41-101).*
Green et al. (Cytokine Growth Factor Rev. Jun. 2016; 29: 109-15).*
Köksal et al. (Tuberk. Toraks. 2006; 54 (1): 17-21).*
Clay et al., "Assays for Monitoring Cellular Immune Responses to Active Immunotherapy of Cancer," *Clinical Cancer Research* 7:1127-1135, May 2001.
Database WPI Week 200103, XP-002701571, 2015, 1 page (corresponds to CN 1262131 A).
Fujita et al., "Induction of Interferons (IFNs) and Tumor Necrosis Factor (TNF) in Mice by a Novel Glycolipid Trehalose 2,3,6'-Trimycolate from *Rhodococcus aurantiacus* (*Gordona aurantiaca*)," *Microbiol. Immunol.* 34(6):523-532, 1990.

(Continued)

*Primary Examiner* — Stephen L Rawlings
(74) *Attorney, Agent, or Firm* — Seed IP Law Group LLP

(57) ABSTRACT

This disclosure relates generally to the field of immunological-based diagnostic assays including an assay to measure cell-mediated immunoresponsiveness. The present disclosure teaches diagnosis of a subject's exposure to an antigen based on cell-mediated immunoresponsiveness with enhanced sensitivity which is achieved by adding a non-reducing sugar during incubation of the sample with the antigen.

14 Claims, 3 Drawing Sheets

(56) References Cited

OTHER PUBLICATIONS

Kruhøffer et al., "Technical Advance: Isolation of Microarray-Grade Total RNA, MicroRNA, and DNA from a Single PAXgene Blood RNA Tube," *Journal of Molecular Diagnostics* 9(4):452-458, Sep. 2007.

Roser, "Trehalose Drying: A Novel Replacement for Freeze-Drying," *Biopharm* 4(8):47-53, 1991.

Xu et al., "Quality Control of Immunocytologic Testing: Prolonged Preservation of Cell Surface Antigen Reactivity With Magnesium Chloride-Sucrose Solution," *Arch Pathol Lab Med* 117(11):1174-1177, Nov. 1993.

* cited by examiner

CELL MEDIATED IMMUNE RESPONSE ASSAY

FIELD OF THE INVENTION

This disclosure relates generally to the field of immunological-based assays and describes methods for measuring cell-mediated immunoresponsiveness. The present disclosure teaches methods, compositions and kits for measuring cell-mediated immune response activity with enhanced sensitivity and improved storage stability.

BACKGROUND OF THE INVENTION

Immunological-based diagnostic assays have a wide application in the medical field. In particular, they are important tools as an aid in detecting and monitoring a variety of disease conditions. The effectiveness of these types of assays lies in part in the specificity of components within the immune system such as T-lymphocytes. Notwithstanding this specificity, immunological-based diagnostics are not necessarily always sensitive enough to detect low grade infections, the presence of a persistent low level infection, to detect infections in subjects with active or latent infectious disease states or in subjects exhibiting immunodeficiency or any form of immunosuppression. Desirable performance characteristics of a cell mediated immune response assay, in particular for detecting an antigen specific T-cell response, include adequate sensitivity, specificity, reliability and reproducibility and furthermore, should be simple and rapid to perform.

One established form of an immunological-based diagnostic assay involves the stimulation of T-cells or other cells of the immune system with antigens followed by the detection of immune effector molecules such as IFN-gamma or other cytokines produced in response to the stimulation with the antigen. The immune effector molecules are detected using well-known techniques such as enzyme immunoassays, multiplex bead analysis, ELISA, ELISpot and flow cytometry. The presence or increase in the level of immune effector molecules can also be determined based on the RNA level. Such assays are e.g. useful for detecting disease-specific immune responses, in particular pathogen specific immune responses. Respective assays are commercially available under the trademark QuantiFERON (Registered Trademark; Cellestis Limited) and can be e.g. used to diagnose a pathogen infection or to monitor cell-mediated immunity against a disease.

Other applications of respective cell-mediated immune response assays include the analysis or the monitoring of cellular immune responses to vaccines or immunotherapy, such as e.g. cancer immunotherapy.

There is a great demand for respective assays with enhanced sensitivity. Previously, methods for measuring cell-mediated immune responses were improved by incubating the sample such as a whole blood sample with the antigen in the presence of a simple sugar such as dextrose (see e.g. WO 2004/042396 A1). It was found that simple sugars such as dextrose and glucose increase the production of IFN-gamma by the immune cells and thereby improve the sensitivity of the assay. The use of simple sugars such as glucose and dextrose was believed to be essential to allow the cells to make use of that energy source and thus benefit from the addition of the sugar during incubation with the antigen. Significant increases in the INF-γ level were observed when the simple sugar was directly added to the sample in addition to the antigen. However, to simplify the performance of the method it is preferred to provide ready-to-use reagent compositions and to avoid manual handling steps. Therefore, it would be desirable to provide a single composition which includes the antigen and the simple sugar. Said composition could be provided in a sample collection tube, whereby the sample is directly contacted with the antigen and the simple sugar in the right concentration thereby avoiding handling errors. Here it was found though that the assay activity diminished over time when respective sample collection tubes comprising the antigen and the simple sugar were stored at room temperature or at elevated temperatures. This was found with certain antigens. Therefore, the shelf-life of these kit components is limited and after a certain storage time, the assay provides only low sensitivity or the assay activity is even completely lost. Therefore, respective kits/assay materials, wherein the antigen is conveniently provided together with a simple sugar in one composition, are not storage-stable and thus pose the risk that the assay sensitivity is reduced or even lost over time. This was not seen when the simple sugar was not included together with the antigen in the sample collection tube, but was added separately to the sample for incubation with the antigen.

The object of the present invention is to overcome at least one drawback of the prior art methods. In particular, it is the object of the present invention to provide sensitive and reliable methods for measuring cell-mediated immune responsiveness as well as kits and kit components which are storage-stable.

SUMMARY OF THE INVENTION

The inventors found that adding a non-reducing sugar during incubation of the sample with the antigen surprisingly increases the response levels and thus the sensitivity of the method in a similar fashion as it is seen when a simple sugar such as dextrose and glucose is added during incubation. This was unexpected because it was previously believed that the increase in the sensitivity can only be achieved with simple sugars and thus monosaccharides, which represent reducing sugars. Furthermore, it was surprisingly found that the method may maintain its increased sensitivity even over prolonged storage periods of the assay materials, even if the non-reducing sugar and the antigen are provided in form of a single composition. Therefore, the inventors surprisingly found that the use of a non-reducing sugar instead of a simple sugar significantly increases the storage stability of the assay components while also increasing the response levels and thus may improve the assay sensitivity. Without being bound in theory, it is believed that the non-reducing sugar increases the amount of released immune effector molecules in case of a positive cell-mediated immune response, thereby improving the assay sensitivity. Apparently, the immune effector molecule production is enhanced. Hence, the use of a non-reducing sugar as described herein may also enable earlier detection of immune cell stimulation than would otherwise be possible. The ability to increase the sensitivity of a cell-mediated immune response assay may also enable the use of the less sensitive means of detection of effector molecules and/or the use of smaller sample sizes. Furthermore, these beneficial effects are also achieved after prolonged storage of the assay materials, thereby improving the reliability and reproducibility of the assay.

According to a first aspect, a method is provided for measuring cell-mediated immune response activity, said method comprising (a) providing an incubation composition by contacting a sample comprising immune cells capable of producing immune effector molecules following stimulation by an antigen with at least one antigen and with at least one non-reducing sugar, and (b) detecting the presence or the level of an immune effector molecule.

Said method can be used e.g. in order to measuring the cell-mediated immune response activity in a subject such as a patient. The presence (or absence) or level of the detected immune effector molecule is indicative of the level or capacity of a subject to mount a cell-mediated immune response against the tested antigen.

According to a second aspect, a composition for inducing a cell mediated immune response is provided, said composition comprising a) at least one antigen;
b) at least one non-reducing sugar; and
c) optionally at least one anticoagulant.

A respective composition can be conveniently used in the method according to the first aspect of the invention in order to prepare the incubation composition by contacting the sample comprising the immune cells with said composition.

According to a third aspect, a sample collection vessel is provided which comprises the composition according to the second aspect of the invention. The sample collection vessel can be conveniently used in the method according to the first aspect of the invention. Preferably, the sample collection vessel is an evacuated blood collection tube.

According to a fourth aspect, a kit for measuring cell-mediated immune response activity in a subject is provided, which comprises at least one antigen, at least one non-reducing sugar, at least one sample collection vessel which preferably is a blood collection tube and at least one detection means for at least one immune effector molecule. A respective kit can be used for performing the method according to the first aspect of the present invention.

According to a fifth aspect, the present invention pertains to the use of a non-reducing sugar in an immunological assay for measuring cell-mediated response activity, wherein the addition of the non-reducing sugar increases the release of at least one immune effector molecule, preferably IFN-gamma, from immune cells that respond to the antigen tested in said assay.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
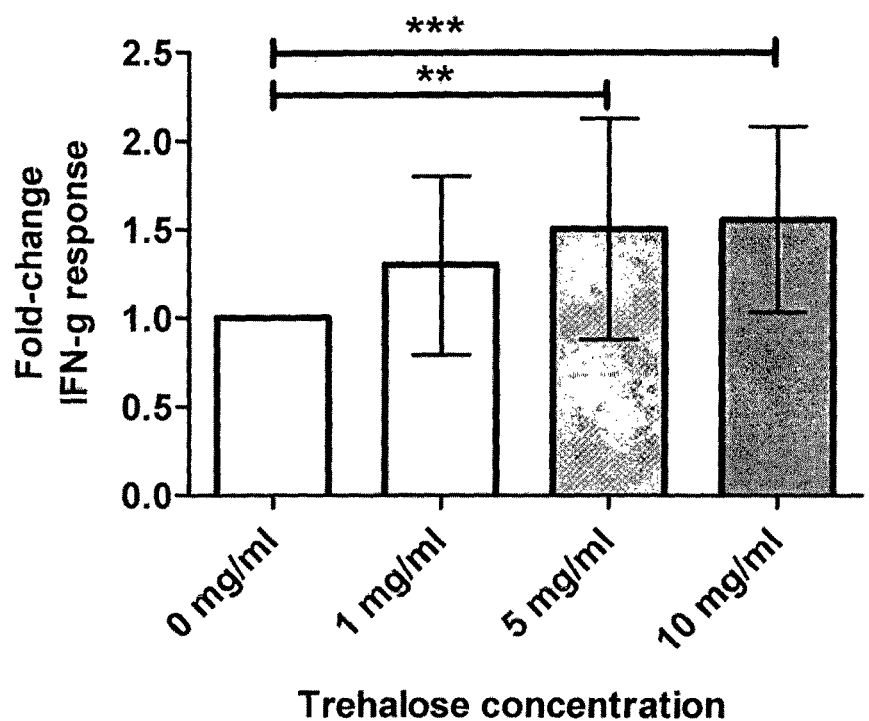
FIG. 1: Effect of trehalose addition on IFN-gamma response in a QFN-CMV assay. ( p<0.01; * p<0.001)

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "a T-cell" includes a single T-cell, as well as two or more T-cells; reference to "an antigen" includes a single antigen, as well as two or more antigens. Likewise, reference to an "agent", "reagent", "molecule" and "compound" includes single entities and combinations of two or more of such entities. Reference to "the disclosure" includes single or multiple aspects taught by the present disclosure; and so forth. Aspects taught herein are encompassed by the term "invention". All aspects of the invention are enabled within the width of the claims.

According to a first aspect, a method is provided for measuring cell-mediated immune response activity, said method comprising (a) providing an incubation composition by contacting a sample comprising immune cells capable of producing immune effector molecules following stimulation by an antigen with at least one antigen and with at least one non-reducing sugar, and (b) detecting the presence or the level of an immune effector molecule.

Advantageous embodiments and applications of said method are described herein. According to one embodiment of the first aspect, a method is provided for measuring cell-mediated immune response activity in a subject, said method comprising (a) providing an incubation composition by contacting a sample comprising immune cells capable of producing immune effector molecules following stimulation by an antigen obtained from a subject with at least one antigen and with at least one non-reducing sugar, and (b) detecting the presence or elevation in the level of an immune effector molecule.

The presence (or absence) or elevated level of the immune effector molecule is indicative of the level or capacity of cell-mediated immune responsiveness of the subject. In particular, said method allows to determine whether said subject has previously encountered the antigen or an antigen for which the tested antigen is representative. Thereby, it can be determined whether the subject is capable of eliciting a cell-mediated immune response against said antigen. In certain embodiments, also the quantitative level of cell-mediated immune responsiveness can be determined. The magnitude of the cell-mediated immune response detected in the assay presently disclosed can in certain embodiments be correlated to a disease state, progression and/or severity of a disease. The refore, the present disclosure provides means to determine the cell-mediated immune responsiveness in a subject. The described method enables and/or supports inter alia the diagnosis of diseases, in particular infectious diseases, pathological conditions, allows to determine the level of immunocompetence and allows assessing of immune cell responsiveness to endogenous or exogenous agents as well as to protein toxicants. The assay also enables screening or monitoring of subjects previously exposed to a particular antigen, such as an antigen associated with a disease, infection or contaminant. Other important applications and utilities of said method will be described subsequently.

The individual method steps and preferred embodiments of the method according to the first aspect of the invention will now be explained in detail.

Step (a)

In step (a), a sample comprising immune cells capable of producing immune effector molecules following stimulation by an antigen is contacted with at least one antigen and with at least one non-reducing sugar. The immune cells and/or the whole sample can be obtained e.g. from a subject whose cell mediated immune responsiveness is to be determined.

Reference to a "subject" includes e.g. a human or non-human species including primates, livestock animals (e.g. sheep, cows, pigs, horses, donkey, goats), laboratory test animals (e.g. mice, rats, rabbits, guinea pigs, hamsters), companion animals (e.g. dogs, cats), avian species (e.g. poultry birds, aviary birds), reptiles and amphibians. The method disclosed herein has applicability in research, human medicine as well as in livestock, veterinary and wild-life applications. Preferably, the subject is a human and the cell-mediated immune response method described herein is used in screening for responsiveness to pathogenic microorganisms, viruses and parasites, disease conditions, potential for development or the monitoring of autoimmune conditions, monitoring a subject's response to oncological challenge or immunotherapy, monitoring cell-mediated immunity against a disease and for determining the presence of any immunodeficiency or immunosuppression. The latter may occur, for example, due to certain medicaments including various chemotherapeutic agents. Alternatively, exposure to environmental proteinaceous toxicants and pollutants can be determined using the method according to the present invention.

The sample comprises immune cells capable of producing immune effector molecules following stimulation with an appropriate antigen. "Immune cells" include but are not limited to lymphocytes including natural killer (NK) cells, T-cells, B-cells, macrophages and monocytes, dendritic cells or any other immune cell which is capable of producing one or more immune effector molecules in response to direct or indirect antigen stimulation. Preferably, the sample comprises lymphocytes, more preferred T-lymphocytes. The terms "T-cells" and "T-lymphocytes" are used interchangeably herein. T-cells are capable of eliciting a strong immune response if they recognize the offered antigen. If the T-cells have been previously exposed to the tested antigen or an antigen for which the tested antigen is representative, a rapid re-stimulation of the T-cells with specific memory of that antigen occurs. These antigen-specific T-cells respond by secreting immune effector molecules such as in particular interferon gamma. Interferon gamma, or an immune effector molecule released in response to the released interferon gamma, can then be measured as specific marker of immune responsiveness against the tested antigen. Therefore, according to one embodiment, the sample comprises T-lymphocytes, preferably $CD4^+$ helper T-cells and/or $CD8^+$ cytotoxic T-cells. Preferably, the sample also comprises corresponding stimulator cells, in particular antigen presenting cells which are capable of presenting the tested antigen to the T-cells. However, suitable antigen presenting cells may also be added separately to the incubation composition. Respectively added antigen presenting cells (APC) include natural as well as artificial antigen presenting cells or particles. E.g. stimulator cells such as irradiated autologous or HLA matched antigen-presenting cells can optionally be separately added to the incubation composition which then present the antigen to T-cells. This embodiment is e.g. feasible if the sample does not comprise respective stimulator cells necessary to induce a T-cell response. Artificial antigen presenting embodiments include but are not limited to particles or lipid vesicles with associated recombinant MHC molecules or peptides and recombinant co-stimulatory molecules.

Preferably, the sample is obtained from a subject. According to one embodiment, the sample is a body fluid comprising immune cells or is an immune cell containing portion derived from a respective body fluid. According to a preferred embodiment, the sample is whole blood. By "whole blood" is meant blood from a subject that has not been substantially diluted or fractionated. According to one embodiment the whole blood sample is peripheral blood. Notwithstanding that whole blood is the preferred and most convenient sample for determining cell-mediated immune response activity, also other samples containing immune cells can be used. Examples include but are not limited to lymph fluid, cerebral, fluid, tissue fluid (such as bone marrow or thymus fluid) and respiratory fluid including nasal and pulmonary fluid and bronchoalveolar lavage. Also portions or derivatives of the above-mentioned samples, e.g. samples depleted of cells unnecessary for measuring the cell mediated immune response may be used as sample and can be obtained by sample processing. For example, whole blood may be treated to remove components unnecessary for the CMI response such as red blood cells and/or platelets by methods known in the art or may be processed to enrich white blood cells. Also buffy coat cells or peripheral blood mononuclear cells (PBMC) can be obtained by methods known in the art and can be used as sample. According to one embodiment, cultured immune cells are used as sample. Furthermore, also cryopreserved cells, e.g. cryopreserved PBMC cells, can be used as source of the immune cells of the subject and thus as sample. E.g. thawed PBMC cells can be contacted with culture medium to provide the sample comprising immune cells which is then contacted and incubated with an antigen and the non-reducing sugar which preferably are added in form of a single composition. According to one embodiment, the sample comprises all immune cells necessary for mediating a cellular immune response. However, as described above, it is also within the scope of the present invention to separately add stimulator cells, in particular antigen presenting cells. According to one embodiment, the sample comprises at least T-cells (T-lymphocytes) and NK cells (NK-lymphocytes). According to one embodiment, the sample is not diluted by more than 50%, 40%, 30%, 25%, 20%, 15%, 10%, 5% or 3% prior to contacting the sample with the antigen and/or the non-reducing sugar.

The sample to be analysed is contacted with at least one antigen and with at least one non-reducing sugar to provide an incubation composition.

The term "antigen" as used herein in particular refers to any molecule or agent that is capable of stimulating or re-stimulating an immune response, and in particular is capable of stimulating or re-stimulating a cellular immune response. Thus, the term "antigen" is used in a broad sense. The term in particular refers to any molecule or agent that can be bound by a major histocompatibility complex (MHC) and can be presented to a T-cell receptor or can be bound by an antibody. The term may also refer to any molecule or agent that can be bound by non-classical WIC proteins such as e.g. CD1d or other CD1 family members. According to one embodiment, the antigen is an immunogen. According to one embodiment, the antigen is not an immunogen. Antigens include but are not limited to peptides, proteins, haptens, allergens or toxins or any naturally occurring or synthetic molecule or parts thereof. According to one embodiment, the antigen is an inactive pathogen or a portion or lysate thereof. According to one embodiment, the antigen is selected from the group consisting of peptides, proteins, including glycoproteins, carbohydrates, phospholipids, phosphoproteins, phospholipoproteins, and fragments of the foregoing. The term "peptide" as used herein also includes polypeptides and proteins unless the context clearly indicates otherwise. The term "protein" also includes modified forms such as glycoproteins and phosphoproteins. According to one embodiment, the antigen comprises one or more full length or part length peptides. According to one embodiment, the antigen is provided by a peptide. According to one embodiment, the one or more peptides used as antigen have a length selected from 5 to 100 amino acids, preferably 7 to 50 amino acids. According to one embodiment, the antigen is provided by a set of peptides from one or more different full length or part length peptides. A peptide set comprises at least two peptides and includes in an embodiment a series of overlapping or non-overlapping peptides. A respective set of peptides may cover the entire length of or a part of a naturally occurring protein antigen. However, the peptides do not necessarily have to be overlapping or may overlap by a single amino acid or by multiple amino acids. According to one embodiment, a peptide set is used which encompasses from 80-100% of a naturally occurring peptide or protein antigen.

According to one embodiment, the antigen is provided by at least one peptide that is recognized by a $CD8^+$ cytotoxic T-cell. For this embodiment, the antigen preferably is provided by at, least one peptide having a length of less than 15 amino acids, preferably 13 amino acids or less, 12 amino acids or less, 11 amino acids or less or 10 amino acids or less. Suitable size ranges for a respective peptide that is recognized by a $CD8^+$ cytotoxic T-cell include 7-14 amino acid residues, 7-13 amino acid residues, 8 to 12 amino acid residues, 8-11 amino acid residues and 8 to 10 amino acid residues. Also a set of peptides can be used which comprises or consists of peptides that are recognized by $CD8^+$ cytotoxic T-cells. Said peptides may encompass all or a part of a protein antigen such as a naturally occurring protein antigen. It was found that assays which incorporate respective short peptides as antigen show a significant decrease in the assay activity during storage in the presence of simple sugars such as glucose or dextrose. This is not seen when using non-reducing sugars as taught by the present invention. Here, the assay sensitivity remains to be increased due to the incorporation of the non-reducing sugar even after prolonged storage time of the assay components. This is an important advantage when using a composition comprising a peptide antigen that is recognized by a $CD8^+$ cytotoxic T-cell and a non-reducing sugar e.g. as kit compound, respectively component.

According to one embodiment, the antigen is provided by at least two sets of peptides, a first set comprising at least one peptide of from about 7 to 14 amino acid residues in length and a second set comprising at least one peptide of from 15 amino acid residues or greater which peptides encompass all or part of a protein antigen. Each respective set comprises from at least one peptide to a series of overlapping or non-overlapping peptides. The co-incubation of the 7 to 14 amino acid peptides and the a 15 amino acid peptides derived from or corresponding to a protein antigen representative for the disease or condition to be tested with the immune cells comprised in the sample results in a more sensitive assay, thereby enabling earlier detection of immune cell and in particular lymphocyte stimulation than would otherwise be possible. The ability to increase the sensitivity of a cell-mediated immune response assay advantageously reduces the detection limit and/or allows the use of less sensitive means for detecting the effector molecules. Therefore, using at least two sets of respective peptides in combination with a non-reducing sugar is beneficial. Without being bound in theory or mode of action, it is believed that the two sets of peptides, the 7 to 14 mer peptides and ≥5 mer peptides, enable detection by both $CD4^+$ and $CD8^+$ T-cells. The $CD4^+$ T-cells recognize the >15 mer peptides and the $CD8^+$ T-cells recognize the 7 to 14 mer peptides. These peptides may be referred to herein as "$CD4^+$ peptides" (≥15 mer peptides) or "$CD8^+$ peptides" (7 to 14 mer peptides). Each set comprises at least one peptide and includes in an embodiment a series of overlapping peptides. Hence, a first set may contain a series of overlapping peptides of from 7 to 14 amino acid residues in length. These peptides are recognized by $CD8^+$ T-cells, ($CD8^+$ peptides). A second set may contain a series of overlapping peptides of greater than 15 amino acid residues in length. These peptides are recognized by cytotoxic $CD4^+$ T-cells ($CD4^+$ peptides). Both sets of peptides may cover the entire length of or a part of a protein antigen, e.g. a naturally occurring protein antigen representative for the disease or condition to be tested. The peptides do not necessarily have to be overlapping or may overlap by a single amino acid or multiple amino acids. The peptides include pods of peptides which encompass and thus cover from 80-100% of a protein antigen. From "80-100%" means 80, 81, 82, 83, 84, 85, 86, 87, 88, 89, 90, 91, 92, 93, 94, 95, 96, 97, 98, 99 or 100%. Reference to a series of overlapping peptides from about 7 to 14 amino acid residues in length which encompass all or part of a protein antigen according to one embodiment means a peptide of from about 7 amino acid residues in length to a maximum of 14 amino acid residues which in total span from every amino acid residues which in total span amino acid residues to up to 6 amino acid residues of a protein antigen from its N-terminal end to its C-terminal end or part thereof. Hence, if the length of a given peptide is x amino acid residues in length wherein x is from about 7 to 14, then the extent of overlap between two consecutive peptides is from x-1 to x-6. In an embodiment, the overlap of each consecutive peptide is x-1. A series of overlapping peptides of ≥15 amino acid residues in length also spans all or part of a protein antigen wherein each peptide is at least 15 amino acid residues in length or up to the length of the full protein antigen. In an embodiment, a peptide of ≥15 amino acid residues in length is from 15 to 50 amino acids such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues.

The present disclosure includes the case where each peptide in the series or peptide set is the same length (i.e. x). However, the series of peptides or peptide set may comprise a mixture of $x_1, x_2, x_j \ldots x_i$ peptides where according to one embodiment each of $x_i$ peptides is from about 7 to 14 amino acid residues in length or ≥15 amino acid residues in length. The $CD4^+$ and/or $CD8^+$ peptides can be divided into separate pools of peptides. They can be added separately to the sample or can be included in one composition, preferably together with the non-reducing sugar. This composition can then be contacted with the sample to prepare the incubation composition.

In some embodiments, one or more antigens are employed which mimic one or more of the effects of antigens presented to the immune system in vivo. According to one embodiment, the antigen is selected from a self-antigen, an antigen derived from or being cross-reactive with an antigen from a pathogenic organism, a metal or inorganic molecule stimulating immune response or a tumor associated antigen. According to one embodiment, the antigen is derived from and thus is cross-reactive with an antigen from a pathogen associated with a disease condition, or is a tumor associated antigen associated with a cancer, or is a or is derived from a toxicant. According to one embodiment, the sample is contacted with an antigen which is specific for the disease or condition for which the cell-mediated immune response is to be tested, e.g. an antigen associated with or representative for a disease or condition to be assessed. According to one embodiment, the antigen is a disease specific antigen, in particular a pathogen specific antigen. In some embodiments, the pathogen is a bacterium, a virus, a parasite or a fungus. In one illustrative embodiment, the antigen is an antigen from a *mycobacterium*, in particular *Mycobacterium tuberculosis*. Therefore, in some embodiments, the antigen is a tuberculosis (TB)-specific antigen. E.g. the antigen can be a purified protein derivative from *Mycobacterium tuberculosis* or *M. avium*. In some embodiments, the antigen simulates mycobacterial proteins such as ESAT-6, CFP-10 and TB7, respectively TB7.7. In another illustrative embodiment, the antigen is from or is specific for a virus such as cytomegalovirus (CMV).

Further examples of antigens, in particular disease specific antigens, are also described subsequently.

Additionally, the sample is contacted in step a) with a non-reducing sugar. A "non-reducing sugar" in particular refers to a sugar which does not react with a detection reagent for reducing sugars, such as Fehling's solution, Benedict's reagent or Tollens' reagent. A non-reducing sugar does not comprise a free reducing end and accordingly, does not comprise a free aldehyde or free ketone group. The non-reducing sugar may have any length and may be linear or branched. In certain embodiments, the non-reducing sugar comprises at least two monosaccharide units. According to one embodiment, in any and all of the monosaccharide units of the non-reducing sugar the carbon atoms neighboring the oxygen atom in the ring structure do not comprise a hydroxyl group and thus, do not comprise an anomeric hydroxyl group. According to one embodiment, the ring structures of the monosaccharide units of the non-reducing oligosaccharide do not comprise a hemiacetal or hemiketal group. According to one embodiment, the non-reducing sugar is an oligosaccharide which comprises 10 monosaccharide units or less, more preferably 8 monosaccharide units or less, 6 monosaccharide units or less, 5 monosaccharide units or less, 4 monosaccharide units or less, 3 monosaccharide units or less or 2 monosaccharide units. Preferably, the non-reducing sugar is a disaccharide. According to one embodiment, the glycosydic bonds are formed between the monosaccharide units by attaching the reducing end of one monosaccharide unit to the reducing end of another monosaccharide unit. Preferred examples of the non-reducing sugar are sucrose and trehalose. Furthermore, as is shown by the examples, mannitol and raffinose may also be used as non-reducing sugar. Thus, according to one embodiment, the non-reducing sugar is selected from trehalose, mannitol, sucrose and raffinose. As is demonstrated by the examples, these exemplary non-reducing sugars increase the magnitude of the response. Trehalose is particularly preferred because experiments show that trehalose increases the magnitude of response and thus may increase the assay sensitivity and furthermore, a composition comprising trehalose and an antigen shows excellent storage stability. As is demonstrated by the examples, among the non-reducing sugars tested, the response increasing effect was strongest with trehalose. However, the non-reducing sugar can also be a monosaccharide, wherein, e.g., the reducing end is coupled to and thereby blocked by another chemical entity. Accordingly, the non-reducing sugar may be derivatized. Examples of sugar derivatives are aminosugars wherein one or more hydroxyl group is substituted by an amino group or an acetylamino group. In preferred embodiments, the non-reducing sugar is not substituted and in particular is not derivatized. According to one embodiment, the non-reducing sugar is not a polysaccharide. In certain embodiments, the non-reducing sugar is not bound to a protein, peptide or lipid or other macromolecule. According to one embodiment, the non-reducing sugar is not comprised in a cell culture medium or other medium. According to one embodiment, the non-reducing sugar is not comprised in a liquid. The non-reducing sugar is metabolizable by immune cells comprised in the sample. According to one embodiment, the non-reducing sugar is a non-reducing sugar which when present in an appropriate concentration in the incubation composition comprising the sample and the antigen is capable of increasing the release of interferon gamma by re-stimulated T-cells.

By contacting the sample with the antigen, the non-reducing sugar and optionally further additives, an incubation composition is provided. Preferably, said incubation composition is incubated above room temperature and thus at elevated temperatures. Preferably, the incubation temperature is above 30° C., preferably above 35° C. Suitable ranges for the incubation temperature include 30° C. to 40° C., preferably 35° C. to 40° C. Conveniently, the incubation composition is incubated at 37° C.+/−1° C. Preferably, the incubation composition is incubated for at least 2 hours at such elevated temperatures to allow stimulation of the immune cells by the antigen and the production of immune effector molecules. The incubation step may be from 2 to 50 hours, such as 2 to 40 hours, 5 to 30 hours, 8 to 24 hours, 16 to 24 hours, or a time period in between including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 hours. In some embodiments, after an optional initial mixing step to distribute the antigen(s), the non-reducing sugar and the sample throughout the incubating composition, incubation is carried out without mixing further.

In the incubation composition, the non-reducing sugar is present in a concentration, wherein it is effective to enhance the stimulation, respectively re-stimulation of the cells of the immune system by the antigen. Therefore, the non-reducing sugar is added in a concentration wherein in a positive sample, i.e. a sample which is immunoresponsive to the antigen, the addition of the non-reducing sugar to the incubation composition increases the level of produced immune effector molecules, preferably interferon gamma, compared to if the non-reducing sugar is not added. Thus, the non-reducing sugar is added in a concentration wherein it enhances the immune effector molecule response magnitude as more immune effector molecules are produced in a sample that shows a cell-mediated immune response. Preferably, the non-reducing sugar is used in a concentration wherein it enhances the immune effector molecule response by at least 1.1 fold, preferably by at least 1.2 fold, more preferred by at least 1.3 fold. According to one embodiment, the non-reducing sugar maintains the ability of the immune cells comprised in the sample to mediate a respective response over prolonged time periods. According to one embodiment, the concentration of the non-reducing sugar in the incubation composition is at least 1 mg/ml, at least 1.5 mg/ml, preferably at least 1.75 mg/ml, more preferred at least 2 mg/ml. Exemplary ranges include but are not limited to 1 mg/ml to 20 mg/ml, 1.5 mg/ml to 17.5 mg/ml, 2 mg/ml to 15 mg/ml, 3 mg/ml to 15 mg/ml, 4 mg/ml to 12.5 mg/ml and 5 mg/ml to 10 mg/ml. As is shown by the examples, these ranges are e.g. suitable for trehalose. They are also suitable for other non-reducing sugars such as sucrose, mannitol and raffinose as is demonstrated by the examples. According to one embodiment, the concentration of the non-reducing sugar in the incubation composition lies in a range of 1.5 mg/ml to 10 mg/ml, e.g. 1.75 mg/ml to 7.5 mg/ml or 2 mg/ml to 5 mg/ml. Suitable concentrations can also be determined by the skilled person following the teachings described herein.

One or more further additives can be added and thus be included in the incubation composition. E.g. one or more additives can be added that are necessary or advantageous for sample preparation and/or sample preservation such as e.g. a suitable anticoagulant if the sample is a blood sample. Preferably, the anticoagulant is heparin. Additives should not be comprised in a concentration wherein they could interfere with the cell-mediated immune response. According to one embodiment, no simple sugar is added to the incubation composition in addition to the non-reducing sugar. According to one embodiment, no reducing sugar, in particular no reducing monosaccharide is added to the incubation composition in addition to the non-reducing sugar.

According to one embodiment, the sample is contacted with a composition which comprises the antigen and the non-reducing sugar. This embodiment is particularly advantageous, because the user does not have to add the non-reducing sugar separately to the incubation composition. To provide such ready-to-use compositions avoids handling errors and saves hands on time. Optionally, a diluent or solvent is comprised in the composition comprising the antigen and the non-reducing sugar. Furthermore, one or more additives can be included in said composition if they are to be included in the incubation composition. The additives should not interfere with the cell-mediated response. According to one embodiment, the composition additionally comprises an anticoagulant, preferably heparin. According to one embodiment, the composition does not comprise a simple sugar. According to one embodiment, the composition does not comprise a reducing sugar, in particular it does not comprise a reducing monosaccharide.

To prepare the incubation composition, the composition comprising the antigen, the non-reducing sugar and optionally comprising one or more further additives such as an anticoagulant in case of a blood sample, is contacted with the sample. The sample can be added to the composition or vice versa. For preparing the incubation composition, the sample, the antigen, the non-reducing sugar and the further additive (if present) preferably is mixed.

Examples of suitable composition forms include liquid compositions, semi-liquid compositions, gel-like composition and solid compositions, in particular dried compositions. According to one embodiment, the composition comprising the antigen, the non-reducing sugar and optionally a further additive is comprised in a sample collection vessel, preferably a sample collection tube such as a blood collection tube. This is particularly convenient as the sample is directly contacted with the composition upon collection. According to one embodiment, the composition comprising the antigen, the non-reducing sugar and optionally a further additive is spray-dried to the interior of the sample collection vessel. Spray-drying methods are well-known in the prior art and therefore, do not need any detailed description here.

According to one embodiment, the sample is obtained from a subject and is not diluted such as e.g. with tissue culture, medium, excipients or other liquid agents prior to contact with the non-reducing sugar and/or the antigen. According to one embodiment, the incubation composition comprises at least 10% by volume sample. The term "at least 10% by volume" includes sample volumes of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by volume of total incubation composition volume.

As is shown by the examples, adding a non-reducing sugar in step a) surprisingly increases the release of immune effector molecules, such as in particular interferon gamma, thereby increasing the sensitivity of the assay. This effect was highly surprising as so far it was believed that this effect can only be achieved by simple sugars and thus by reducing monosaccharides. Furthermore, it was found that compositions comprising the antigen and a non-reducing sugar show an improved storage-stability even at elevated temperatures. The effect observed with reducing sugars that the assay sensitivity and quality may diminish over time is not seen with non-reducing sugars. Therefore, the present invention makes an important contribution to the prior art by providing a sensitive and storage-stable assay which maintains the assay performance also over prolonged storage periods. The teaching of the present invention conveniently allows to provide the antigen and the non-reducing sugar in form of a storage-stable composition. In the present invention, the non-reducing sugar is not used as stabilizer for the antigen. It was shown by experiments that antigens, in particular peptide antigens, are very storage stable. Therefore, no decrease in the assay performance is seen if the antigen is stored in the absence of a sugar. Therefore, the non-reducing sugar is used to enhance the assay sensitivity, in particular by enhancing the production and/or release of immune effector molecules, in particular of cytokines such as interferon gamma.

Step (b)

In step (b), the presence or elevation in the level of an immune effector molecule is detected. As described above, the presence (which includes the absence) or level of an immune effector molecule is indicative of the level or capacity of cell-mediated immune responsiveness of the subject against the tested antigen. In particular, said method allows to determine whether said subject has previously encountered the tested antigen or an antigen that shows cross-reactivity with the tested antigen such as the pathogen to be detected Thereby, it can be determined whether the subject is capable of eliciting a cell-mediated immune response against said antigen, respectively the antigen, pathogen or disease the tested antigen is representative for.

The detection of the immune effector molecule may occur at the peptide or protein level or at the nucleic acid level, in particular, the immune effector molecule mRNA expression level. Consequently, reference to detecting the "presence or level" of the immune effector molecule includes direct and indirect data. For example, the presence or amount of immune effector molecules can be directly determined using appropriate detection methods such as ELISA or ELISpot. However, in one embodiment, the presence or level of the immune effector molecule is measured based on its RNA expression level. High levels of immune effector molecule mRNA are indirect data showing increased levels of the immune effector molecule. Suitable methods for determining the mRNA expression level of a target gene are well-known in the prior art and therefore, do not need any detailed description. Accordingly, in some embodiments, the immune effector molecule may be detected using ligands or binding molecules such as antibodies specific for the effector molecule or by measuring the level of expression of genes encoding the immune effector molecule.

The immune effector molecules to be detected may be any of a range of molecules which are produced in response to cell activation, stimulation or re-stimulation by an antigen. Also, more than one immune effector molecule or a pattern of immune effector molecules released upon contact of the sample with the tested antigen can be detected in step (b). The immune effector molecule to be measured may be produced by immune cells, in particular can be produced by lymphocytes such as T-cells, in particular CD4$^+$ helper T-cells and/or CD8$^+$ cytotoxic T-cells. Thus, in some embodiments, the method is based upon measuring the production of one or more immune effector molecules by cells of the immune system, in particular T-cells, in response to antigenic stimulation. However, also non-immune cells may release immune effector molecules in response to stimulation, respectively re-stimulation, of immune cells by the antigen as they are stimulated by the immune effector molecules that are released by the immune cells, in particular by immune effector molecules such as IFN-gamma released by re-stimulated T-cells. These immune effector molecules can also be an important source of information. Therefore, according to an embodiment, the immune effector molecule to be detected may be the immediate effector molecule produced by effector T cells in response to antigen re-stimulation. In other embodiments, a downstream immune effector molecule is measured. For example, IFN-gamma or other immediate immune effector molecules produced by immune cells, in particular by T-cells that are (re)stimulated by the tested antigen, can be measured in step (b). However, as described above, these molecules often induce or enhance the production of further immune effector molecules by other cells. The production of these further (downstream) immune effector molecules may also be measured in step (b). The present invention also encompasses detecting more than one type of immune effector molecule in step (b). According to one embodiment, the presence or level of a pattern of immune effector molecules is detected in step (b) either alone or in addition to immediate immune effector molecules such as IFN-gamma. A respective pattern comprises more than two, preferably more than three different immune effector molecules. Analyzing a respective pattern can provide valuable information of the immune status of the subject. E. g. specific immune effector molecules or patterns of immune effector molecules can be characteristic for specific diseases.

According to one embodiment, the immune effector molecule to be measured in step (b) is a cytokine such as a lymphokine, interleukin or chemokine. An interferon (IFN) such as IFN-gamma is a particularly useful as immune effector molecule to be determined. Other examples of immune effector molecules include, but are not limited to a range of cytokines such as interleukins (IL), e.g. IL-2, IL-4, IL-6, IL-8 (CXCL8), IL-10, IL-12, IL-13, IL-16 (LCF) or IL-17, IL-1α (IL-1F1), IL-1β (IL-1F2), IL-1rα (IL-1F3), Tumor Necrosis Factor alpha (TNF-α), Transforming Growth Factor beta (TGF-β), a Colony Stimulating Factor (CSF) such as Granulocyte (G)-CSF or Granulocyte Macrophage (GM)-CSF, complement component 5a (C5a), Groα (CXCL1), sICAM-1 (CD54), IP-10 (CXCL10), I-TAC (CXCL11), MCP-1 (CCL2), MIF (GIF), MIP-1α (CCL3), MIP-1β (CCL4), Serpin E1 (PAI-1), RANTES (CCL5) or MIG (CXCL9). In some embodiments, the present invention provides methods wherein the immune effector molecule to be detected in step (b) is a cytokine, a component of the complement system, perforin, defensin, cathelicidin, granzyme, Fas ligand, CD-40 ligand, exotaxin, a cytotoxin, a chemokine or a monokine. In preferred embodiments, the immune effector molecule detected in step (b) is IFN-gamma. Thus, according to a preferred embodiment, the present invention provides a method for measuring a cell mediated immune response in a subject, said method comprising collecting a sample from said subject into a collection vessel wherein said sample comprises cells of the immune system which are capable of producing IFN-gamma following stimulation by an antigen, incubating said sample with an antigen and a non-reducing sugar and then measuring the presence of or elevation in the level of an IFN-gamma wherein the presence or level of IFN-gamma is indicative of the capacity of said subject to mount a cell-mediated immune response.

Also a combination of immune effector molecules can be detected in step (b). Thus, step (b) in particular comprises detecting an immune effector molecule or combination of immune effector molecules, in particular cytokines, released in response to the stimulation with the antigen and characteristic for the disease or condition to be analyzed. Furthermore, the level of the one or more immune effector molecule may be screened alone or in combination with other biomarkers or disease indicators.

According to one embodiment, the immune effector molecule is detected by using a ligand which specifically binds the immune effector Molecule. Ligands to the immune effectors are particularly useful in detecting and/or quantitating these molecules. Cells comprised in the incubation composition can be removed prior to detecting the immune effector molecule. Techniques for the detection assays that can be used in step (b) are known in the art and include, for example, radioimmunoassays, sandwich assays, ELISA and ELISpot. Antibodies to the immune effectors are particularly useful as ligands. Reference to "antibodies" includes parts of antibodies specifically binding the immune effector molecule such as Fab fragments, mammalianized (e.g. humanized) antibodies, deimmunized antibodies, recombinant or synthetic antibodies and hybrid and single chain antibodies. Both polyclonal and monoclonal antibodies are obtainable by immunization with the immune effector molecules or antigenic fragments thereof and either type is utilizable for immunoassays. Methods of obtaining both types of antibodies are well known in the art. Polyclonal antibodies are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favored because of the potential heterogeneity of the product. The use of monoclonal antibodies in an immunoassay is particularly useful because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. Antibodies against specific immune effector molecules are also commercially available According to one embodiment, step (b) comprises contacting the incubation composition or a portion thereof, such as e.g. a cell-depleted portion thereof, with an antibody or a fragment thereof specific for the immune effector molecule to be detected for a time and under conditions sufficient for an antibody-effector complex to form, and then detecting said complex. As described above, cells comprised in the incubation composition may be removed e.g. by centrifugation prior to detection. E. g. when using blood as sample, cells can be separated from the incubation composition after incubation and thus production and release of immune effector molecules prior to detection, thereby basically providing a plasma sample.

A wide range of immunoassay techniques are available as can be seen by reference to U.S. Pat. Nos. 4,016,043, 4,424,279 and 4,018,653. Respective assays that can be used in conjunction with cell-mediated immune response tests described herein to detect the produced immune effector molecules are also described in WO2004/042396, WO2008/113119, WO2010/009494 and WO2011/075773, herein incorporated by reference. Also Clay et al. "Assays for monitoring cellular immune responses to active immunotherapy of cancer; Clinical Cancer Research 2001; 7:1127-1135" describe several methods for monitoring cellular immune responses, thereby also describing suitable assays for detecting the immune effector molecules produced in response to antigen (re)stimulation. Therein, e.g. ELISA-based assays, ELISpot assays and nucleic acid-based assays such as the measurement of cytokine mRNA levels by real-time quantitative RT-PCR are described. Optionally, when determining the level of immune effector molecule based on its RNA expression level, the obtained data can be normalized to the expression of control gene, such as for example CD8. Respective methods can also be used in conjunction with the present invention to detect the produced immune effector molecules. According to one embodiment, a nucleic acid based assay for detecting the presence or level of an immune effector molecule is used. Nucleic acids, in particular RNA, can be isolated from the incubation composition or the cellular portion thereof using standard methods well-known in the prior art. Preferably, the presence or elevation of the expression of the immune effector molecule is detected in this embodiment using amplification based assays, preferably PCR based assays. Isolated RNA can first be reverse transcribed to cDNA prior to amplification using primers and/or probes specific for the immune effector molecule to be detected. Preferably, the detection is quantitative. One suitable method is quantitative real-time RT (reverse transcription) PCR.

Preferably, the detection of the immune effector molecule in step (b) is a quantitative detection.

SPECIFIC EMBODIMENTS

Specific and preferred embodiments of the method according to the present invention and components used therein will we be described in the following.

As described above, in step (a), one or more additional additives may be included in the incubation composition. According to one embodiment, an agent is added to the incubation composition to modulate the activity of regulatory T-cells (T-reg cells). The latter encompasses inhibiting the suppressor function of T-reg cells. Agents which modulate T-reg cells encompassed herein include but are not limited to a CD25 ligand, a sense or antisense oligonucleotide to genetic material encoding JAK1 or TYK2, a neutralizing antibody, a CpG containing oligonucleotides, an oligonucleotide acting as a toll-like receptor (TLR) modulating agent, and other TLR modulating agents. In a particular embodiment, the T-reg cells are immune response suppressor cells the activity of which is inhibited by the modulating agent. A "CpG molecule" means an oligonucleotide comprising a CpG sequence or motif. Examples of inhibitors or modulators of T-reg function include CD25 ligands including but not limited to a polyclonal or monoclonal antibody to CD25 or an antigen-binding fragment thereof, humanized or deimmunized polyclonal or monoclonal antibodies to CD25 or a recombinant or synthetic form of the polyclonal or monoclonal antibodies. Other examples of agents include sense or antisense nucleic and molecules directed to the mRNA or DNA encoding Janus Tyrosine Kinase 1 (JAK1) or Tyrosine Kinase 2 (TYK2) or small molecule inhibitors of JAK1 or TYK2 proteins. Reference to "small molecules" includes immunoglobulin new antigen receptors (IgNARs) as described in International Patent Publication No. WO 2005/118629. Yet still further examples of suitable agents stimulating agents such as CpG molecules which act via Toll-like receptors (TLRs) and/or other mechanisms. Hence, CpG containing oligonucleotides and an oligonucleotide acting as a TLR modulating agent also form part of the present disclosure. A single type of agent may be used or two or more types of agents may be employed to modulate T-reg cells. For example, the assay may be conducted with a CD25 ligand and a JAK1/TYK2 sense or antisense oligonucleotide; a CD25 ligand and a TLR modulating agent; a JAK1/TYK2 sense or antisense oligonucleotide and a TLR modulating agent; or a CD25 ligand, a JAK1/TYK2 sense or antisense oligonucleotide and a TLR modulating agent. Alternatively, just one type of agent is employed. In another alternative, a CpG comprising oligonucleotide and a TLR modulating agent is used. Respective T reg modulating agents may be added separately to the sample and/or the incubation composition or may be included in the composition comprising the antigen and/or the non-reducing sugar.

According to one embodiment, the method according to the present invention comprises (a) preparing an incubation composition by contacting a whole blood sample obtained from a human subject with a composition comprising at least one peptide antigen and at least one non-reducing disaccharide, preferably trehalose or sucrose, and incubating the incubation composition for at least 2 hours above room temperature; and (b) detecting the presence or level of IFN-gamma;

wherein the presence or level of IFN-gamma is indicative of the level of cell-mediated immune responsiveness of the human subject.

Preferably, the peptide antigen is an antigen specific for a disease or pathogen. Non-limiting examples of pathogens are described herein. According to one embodiment, the pathogen is a virus and the method allows to determine whether the human subject has the capacity to mount an anti-viral cell-mediated immune response.

According to one embodiment, the method additionally comprises (c) comparing the detected immune effector molecule level or a value derived therefrom with a reference-level.

Step (c) comprises comparing the determined immune effector molecule level or a value derived therefrom with a reference-level. This embodiment is particularly useful for diagnosing a pathogen infection for which the antigen is representative. If said subject is infected with the pathogen, the determined immune effector molecule level or a value derived therefrom is above the reference-level and if said subject is not infected with the pathogen, the determined immune effector molecule level or a value derived therefrom is below the reference-level. The same principle applies for determining if said subject is capable of mounting a cell mediated immune response against a pathogen for which the antigen is representative.

According to one embodiment, the sample is divided into at least two fractions and in step (a) the first fraction of the sample is contacted with an antigen and a non-reducing sugar to generate a response sample and wherein the second fraction of the sample is contacted with an inactive solution to generate a negative control (nil) sample. In step (b) of this embodiment, the presence or level of the immune effector molecule is determined in the two fractions. In step (c), the antigen-dependent immune effector molecule response of the sample is determined by subtracting the immune effector molecule level determined in the negative control sample from the immune effector molecule level determined in the response sample. The antigen-dependent immune effector molecule response or a value derived therefrom is then compared with a reference-level, thereby providing an aid in determining whether the subject has previously encountered the antigen. Thereby, it can e.g. be determined whether the subject has generated immunological reactivity to the antigen, is at risk of developing a disease and/or is susceptible to an infection with a pathogen.

Optionally, the method may further comprise dividing the sample into at least three fractions and incubating the third fraction of the sample with a T cell activator such as a mitogen to generate a positive control sample. Here, the immune cells may be incubated in e.g. three separate populations; negative control sample (e.g. saline), antigen stimulated response sample and positive control sample (using e.g. a T-cell activator, e.g. a mitogen such as phytohemagglutinin). Thus, according to one embodiment, the sample is divided into at least three fractions. In step (a) the first fraction of the sample is contacted with an antigen and a non-reducing sugar to generate a response sample, the second fraction of the sample is contacted with an inactive solution to generate a negative control sample and the third fraction of the sample is contacted with a stimulatory solution (comprising e.g. a mitogen) to generate a positive control sample. In step (b) of this embodiment, the presence or level of the immune effector molecule is determined in the three fractions. In step (c), the antigen-dependent immune effector molecule response of the response sample is determined by subtracting the immune effector molecule level determined in the negative control sample from the immune effector molecule level determined in the response sample and comparing the antigen-dependent immune effector molecule response or a value derived therefrom with a reference-level; the immune effector molecule response of the positive control sample is determined by subtracting the immune effector molecule level determined in the negative control sample from the immune effector molecule level determined in the positive control sample and comparing the resulting immune effector response with a reference-level or a value derived therefrom. Thereby, it can be determined whether the subject has previously encountered the tested antigen or an antigen which shows cross-reactivity thereto and thus generated immunological reactivity to the antigen. This provides a valuable aid in determining e.g. whether the subject has an active, a recent, or a latent infection, or if the subject is responding to treatment, is going to develop an infection or disease, or is immune-suppressed. E.g. if the antigen-dependent immune effector molecule response is above the reference level, the result can be assessed as being positive, i.e. that the subject is capable of a cell-mediated response against said antigen. if the antigen-dependent immune effector molecule response is below the reference level and the positive control dependent immune effector response is above the reference level, the result can be assessed as being negative, i.e. that the subject is not capable of a cell-mediated response against said antigen.

The mitogens that can be used in the present invention as positive control encompass all mitogens known by the skilled person and include but are not limited to phytohaemagglutinin (PHA), concanavalin A (conA) lipopolysaccharide (LPS) and pokeweed mitogen (PWM). Other examples of immune stimulants besides mitogens that can be used for providing a positive control include but are not limited to chemical compounds such as R848.

As described above, in some embodiments, the vessel in which sample, antigen and non-reducing sugar are co-incubated is also the collection container used to collect the sample from the subject. Any one of a large number of different available containers may be used provided that they provide suitable sample dimensions. In some embodiments, the vessel is a tube which comprises a vacuum to facilitate the collection of the sample such as blood from a subject. Respective evacuated blood collection tubes are well-known in the prior art and thus, do not need any detailed description herein. In other embodiments, the vessel is a capillary tube. In some embodiments, a capillary tube is used to collect blood from the surface of the skin by capillary action. In some embodiments, the sample is collected from a subject into a collection vessel containing at least one antigen, at least one non-reducing sugar and at least one anticoagulant, preferably heparin, or to which an antigen, a non-reducing sugar and an anticoagulant, preferably heparin, is subsequently added. In some embodiments, blood is sampled using a capillary sampling device such as a pin prick device and blood is collected into a heparinised collecting container and subsequently transferred into an appropriate container for co-incubation with the antigen and the non-reducing sugar. Preferably, the antigen, the non-reducing sugar and optionally the anticoagulant are provided in form of a single composition as described above. In some embodiments, whole blood from a subject is collected into a container containing the antigen, the non-reducing sugar and optionally the anti-coagulant. In other embodiments, the antigen, the non-reducing sugar and/or anticoagulant are added to the whole blood sample after collection.

The present invention is particularly useful for screening for exposure to pathogens, in particular mycobacteria such as *M. tuberculosis*. Hence, the present disclosure teaches a method for measuring cell-mediated immune response activity in a subject, the method comprising contacting a sample comprising immune cells capable of producing immune effector molecules following stimulation by an antigen with a tuberculosis specific antigen and with a non-reducing sugar. The peptide(s) used as antigen may encompass all or part of a protein antigen of *M. tuberculosis*. After incubation, the level of an immune effector molecule, preferably interferon gamma, produced by the immune cells is determined wherein the level of the immune effector molecule is indicative of the level of cell-mediated immunoresponsiveness of the subject to *M. tuberculosis*.

ESAT-6 is a six kDa early secretary antigenic target of *M. tuberculosis*. The ESAT-6 protein (early secreted antigenic target 6) is a major secreted antigen which has been purified from *M. tuberculosis* short-term culture filtrates. As referred herein ESAT-6, CFP-10 (culture filtrate protein 10) and 85B can be obtained from cell lysate and purification, by recombinant techniques or produced as synthetic peptides. For example ESAT6 can be obtained as a recombinant protein from Statens Serum Institute (SSI, Copenhagen Denmark). Other suitable target protein antigens for *M. tuberculosis* include TB7.7 and TB37.6. CFP10 is also known as ESAT-6-like protein eesxB and secreted antigenic protein MTSA-10.

Tuberculin or PPD (purified protein derivative) differs from ESAT-6 (early secreted antigenic target 6), CFP-10 (culture filtrate protein 10), and TB7.7 which are encoded by genes (in the RD-I region) located only within the *M. tuberculosis* genome and are not contained in BCG (the Bacille of Calmette et Guerin). It differs from PPD because PPD also contains other antigens that are shared with e.g. BCG sub-strains and with several non-tuberculous mycobacterial species with low or no pathogenicity. According to one embodiment, PDD is used as antigen. Specifically as used herein the term Purified Protein Derivative (PPD or tuberculin) is a precipitate of non-species-specific molecules. PPD or tuberculin is obtained by extracting proteins from a mixture of *M. tuberculosis* or other mycobacteria such as *M. avium*. PPD is commonly employed in testing for the presence of cellular immunity or Thl response generated either against BCG or against *M. tuberculosis*. For example, it can be obtained from the TubersolB of Connaught Laboratories Limited prepared from a large Master Batch, Connaught Tuberculin (CT68), or in the form of RT23 obtained from the Statens Serum Institute (SSI, Copenhagen Denmark).

Preferably, the antigen is selected from CFP10, ESAT-6, TB7.7 and TB37.6 from *Mycobacterium tuberculosis*. According to one embodiment, the antigen is provided by peptides corresponding to these protein antigens and/or showing cross-reactivity thereto.

In an embodiment, the sample is contacted with a combination of CD4$^+$ and CD8$^+$ peptides, which were described in detail above. We refer to the above disclosure.

The cells of the immune system lose the capacity to mount a cell mediated immune response in whole blood after extended periods following blood draw from the subject, and responses without intervention are often severely reduced or absent by 24 hours following blood draw. The reduction of labor and need for specialized equipment in the present invention allows cell mediated immune response stimulation with antigens to be performed at the point of care locations such as physicians' offices, clinics, outpatient facilities and veterinary clinics or on farms. Once antigen stimulation is complete, the requirement for fresh and active cells no longer exists. IFN-gamma and other cytokines or immune effector molecules released due to the stimulation with the antigen are stable in cell-free or cell-depleted fluids such as plasma and, thus, the sample can be stored, or shipped without special conditions or rapid time requirements in a similar fashion to standard plasma or serum samples used for other infectious disease or other disease diagnosis. Therefore, a detection of the actual released immune effector molecules is preferred. However, the cells comprised in the incubation composition or the whole incubation composition can be contacted after incubation with a nucleic acid stabilizing composition which comprises reagents that stabilize the RNA expression pattern if the presence or level of immune effector molecule is determined based on the RNA expression level of the immune effector molecule. Several stabilizing compositions are commercially available. E.g. PreAnalytiX provides compositions that contain reagents for an immediate stabilisation of the RNA gene expression profile in blood.

The respective compositions can also be used to stabilize the RNA gene expression profile of the cells comprised in the incubation composition. The respective stabilisation composition allows the transport and storage at room temperature without the risk of changes in the RNA profile by gene induction and transcript degradation (see for example U.S. Pat. Nos. 6,617,170, 7,270,953, Kruhoffer et al., 2007). The respective compositions are sold under the name of PAXgene Blood RNA Tubes.

Applications, Diseases and Conditions

Non-limiting applications, including uses, diseases and conditions will be described in the following. As is apparent therefrom, the method according to the invention as well as the compositions and kits described herein can be widely used in the medical and diagnostic field and e.g. can be used in in vitro assays suitable for analysing the cell-mediated responsiveness of patients. Furthermore, the method according to the invention as well as the compositions and kits described herein are valuable analytical tools in order to test the capability of agents such as e.g. cancer immunotherapeutics to stimulate and thus enhance cell mediated immunity.

The method taught herein enables e.g. the detection of the presence or absence or level or stage of a disease or condition in a subject such as an infection by a pathogenic agent, an autoimmune disease, cancer, exposure to an inflammatory agent, exposure to a medicament, exposure to a toxic proteinaceous agent and immunodeficiency or immunosuppression conditions such as induced by a disease condition or induced by pharmaceutical agents. The ability to reliably and sensitively measure cell-mediated immunity is e.g. important for assessing a subject's ability to respond to an infection by a pathogenic agent such as a microorganism, virus or parasite, to mount an autoimmune response, to respond to a vaccine or immunotherapeutic, to protect against cancers or other oncological conditions, to detect an inflammatory condition or to detect exposure or sensitivity of a subject to a toxic agent such as beryllium or environmental agents. The assay described herein enables early and/or more sensitive detection of immunoresponsiveness.

The assay described herein also enables and aids to the detection of disease conditions which lead to immunosuppression or to detect an immunosuppression induced by medicaments. Consequently, "measuring a cell-mediated immune response in a subject" as taught herein has many useful applications in the medical field and non-limiting uses and application will be described subsequently.

E.g. the method described herein can be used for immune diagnosis of infectious and autoimmune diseases, as marker for immunocompetence, as well as a marker for inflammatory diseases, allergens, cancer, the effect of immunotherapeutics, and as marker for toxic agents. Furthermore, the method is generally useful for the detection of T-cell responses to endogenous and/or exogenous antigens (including a measure of the efficacy of a vaccine).

Cell-based, functional immune response assays have also gained acceptance as surrogate markers of efficacy in the development of vaccines, immunotherapeutics and biologics that impact immune responses. The assays can be used in academic settings, in pharma settings and in the research and development of vaccines and biologics. Evaluation of functional capacity of immune cells is critical to understanding several disease conditions and the efficacy of therapeutic strategies directed towards them. Immune cells are either responsible for prevention or therapy, for example in infectious diseases like HIV, or responsible for the disease condition itself, for example in autoimmune disease conditions. Self-antigen-specific reactivity can be measured in patients afflicted with an autoimmune disease such as multiple sclerosis using the method according to the present invention. The present invention provides assays that are useful for these purposes.

Numerous cancer immunotherapy strategies are currently being tested in clinical trials. Although clinical efficacy will be the final test of these approaches, the long and complicated development pathway for these items necessitates evaluating immunological responses as intermediate markers of the most likely candidates for success. This has emphasized the need for assays that accurately detect and quantitate T-cell-mediated, antigen-specific immune responses. For respective immunotherapeutic agents, which, e.g., are not necessarily expected to cause tumor regression, but still have a beneficial effect on the disease, a biological marker must be chosen based on the presumed mode of activity. For immunotherapy, such a marker is the stimulation of the tumor antigen-specific immune response detectable by one or more immunological assays. Here, preferably assays are used that evaluate the function of $CD8^+$ cytotoxic T-cells that directly recognize tumor peptides presented by MHC molecules on the surface of a tumor cell as a trigger for direct cytolysis and $CD4^+$ helper T-cells, particularly T helper type 1 responses, that lead to cytotoxic T-cell generation. The present invention provides assays that are useful for that purpose due to their sensitivity and reliability. Thus, the method, kits and compositions described herein can be used to analyze whether a pharmaceutical agent such as e.g. a cancer immunotherapeutic is capable of enhancing cell-mediated immunity. This can be tested e.g. on a general level using available, e.g. standardized, immune cells (examples are described above), or may also be tested in an individual patient in order to analyse whether the specific immunotherapeutic such as e.g. a cancer immunotherapeutic is capable of enhancing cell-mediated immunity in said patient. Such assay is valuable for clinical development as well as in the later therapeutic setting in order to analyse whether a patient benefits from a therapy with an immunotherapeutic. Examples of immunotherapeutics include but are not limited to biologics such as therapeutic antibodies that enhance the activity of T-cells, in particular cytotoxic T-cells. The mode of action is not relevant as long as it results in or is supposed to result in a stimulation/increase of cell-mediated immunity. For example, the activity can be enhanced by direct stimulation of the immune cells or by reducing or turning off inhibitory mechanisms that negatively affect the activity of said T-cells, thereby, also indirectly stimulating/increasing cell-mediated immunity. One example is the cancer immunotherapeutic antibody Ipilimumab.

Furthermore, the method according to the present invention can be used to detect the presence, absence, level or stage of a disease or condition in a subject, wherein the presence or level of the immune effector molecule detected using the method according to the present invention is indicative of the disease or condition.

Furthermore, the method according to the present invention can be used to determine whether an agent or a disease condition induces or is associated with immunosuppression in a subject, wherein the presence or level of the immune effector molecule detected using the method according to the present invention is indicative of the extent of immunosuppression induced by the agent or induced by or associated with the disease condition.

One aspect of the present application includes methods that demonstrate the cell-mediated immune responsiveness of a subject by measuring responsiveness to a particular antigen using the method according to the present invention. In an embodiment, a sample such as whole blood, an enriched white blood cell fraction or bronchoalveolar lavage may be obtained from a subject having or suspected of developing a particular disease (e.g. autoimmune disease, a disease caused by an infection with a pathogenic agent, or exposure to a toxic agent) and the immune responsiveness is measured by using the method according to the first aspect of the present invention e.g. by detecting immune effector molecules released from effector T-cells (e.g. $CD4^+$ T-cells and/or $CD8^+$ cytotoxic T-cells) in response to stimulation by the antigen.

The method of the present invention is particularly useful in detecting and/or monitoring a disease or condition including the level or stage of the disease or condition in a subject such as an infection by a pathogenic agent, an autoimmune disease, cancer or an inflammatory condition. Other conditions include exposure to toxic agents such as beryllium. The assay of the present invention is also useful in monitoring therapeutic protocols.

The presence or level of the immune effector molecule produced in response to the tested antigen is indicative of the level of cell-mediated responsiveness of the subject. In particular the level of responsiveness is indicative of the presence or absence or level or stage of a disease or condition selected from the list comprising an infection by a pathogenic agent, an autoimmune disease, a cancer, an inflammatory condition and exposure to a toxic agent. In particular, the presence or level of the immune effector molecule is indicative of the presence, absence, level or stage of a disease or condition for which the tested antigen is representative.

The method may also be used for monitoring a response to a therapeutic protocol for a disease or condition in a subject. The presence, level or pattern of produced immune effector molecule may be indicative of the efficacy of the therapeutic protocol.

The method of the present invention may also be referred to as an "assay". The method is an ex vivo method. The assay described herein is useful inter alia in assessing the general immune responsiveness of a subject or is useful for detecting the responsiveness to specific disease conditions such as an autoimmune disease, Celiac's disease, cancer or infection by a pathogenic organism or agent, exposure to a toxic agent or medicament and immunodeficiency or immunosuppression conditions such as induced by a disease condition or by a therapeutic agent.

In One embodiment, the subject is a human and the cell-mediated immune response assay is used in screening for responsiveness to pathogenic microorganisms, viruses and parasites, potential for development or monitoring an autoimmune condition, Celiac's disease, monitoring a subject's response to oncological challenge and for determining the presence of any immunodeficiency or immunosuppression. The latter may occur, for example, due to certain medicaments including various chemotherapeutic agents. Alternatively, exposure to environmental toxicants and pollutants can be tested. In an embodiment, disease conditions leading to immunosuppression include chronic infection and cancer. Other disease conditions which can lead to immunosuppression include inflammatory disease conditions.

Medicaments which can lead to immunosuppression include those used to treat rheumatoid arthritis, cancer and inflammatory bowel disease or those given in conjunction with organ transplantation.

In one embodiment, the method described herein may be used for or as an aid in diagnosis or monitoring of subjects suspected of tuberculosis (e.g. active, latent or recent TB infection) and in particular of patients at increased risk for progression from latent to active tuberculosis e.g. in patients receiving immunosuppressing medication (i.e. monoclonal antibody treatment (anti-CD20 antibodies (e.g. Rituximab©) or TNF-alpha blocking treatment (e.g. Remicade©, Enbrel©, Humira©))) or steroids or cancer-chemotherapy; or, patients suffering from immunosuppressing conditions (e.g. HIV infection, cancer, IDDM or non-insulin dependent diabetes mellitus (NIDDM), autoimmune conditions, malnutrition, old age, intravenous drug use (IVDU) or inherited immune disorders), and in individuals who have recently been infected.

In one embodiment, the method described herein may be used for monitoring subjects diagnosed with infections or other disease conditions. This may e.g. help to assess efficacy of treatment during and after termination of a treatment e.g. by monitoring and predicting possible recurrence of the infection.

According to one embodiment, the method is for determining if a subject is infected with and/or is capable of mounting a cell-mediated immune response against a pathogen for which the antigen is representative.

Pathogenic or infectious agents include bacteria, parasites and viruses. Examples of bacteria include Gram positive and Gram negative microorganisms such as *Mycobacterium* species, *Staphylococcus* species, *Streptococcus* species, *Escherichia coli*, *Salmonella* species, *Clostridium* species, *Shigella* species, *Proteus* species, *Bacillus* species, *Hemophilus* species, *Borrelia* species amongst others. *Mycobacterium tuberculosis* is a particularly useful target as well as conditions arising from infection by *M. tuberculosis* such as tuberculosis (TB). Examples of viruses include Hepatitis virus (Hepatitis B virus and Hepatitis C virus), Herpes virus and CMV virus and Human immune deficiency virus (HIV) as well as diseases resulting therefrom. Parasites include *Plasmodium* species, ringworm, liver parasites and the like. Other pathogenic agents include eukaryotic cells such as yeasts and fungi. It is generally important to assess the potential or actual cell-mediated responsiveness in subjects exposed to these infectious entities. The method of the present disclosure can also be used to detect the presence or absence of these infections as well as the level or stage of the disease process.

The method can also be used to monitor the level of the cell-mediated immunity against certain diseases and/or infectious agents in persons that are at risk of developing a respective disease. One example is a CMV infection in immune suppressed patients such as organ transplant patients. CMV infections frequently occur as complication of immunesuppression, particularly after transplantation, and significantly contribute to morbidity and mortality in transplant recipients. Current immunesuppressive therapies used to prevent the rejection of transplanted organ have detrimental effects upon the T lymphocytes and thus cell-mediated immune responses, resulting in increased susceptibility to viral infections post transplant. The importance of T-cell function and suppressing CMV replication is also highlighted by the fact that $CD8^+$ CMV specific cytotoxic T lymphocytes (CTLs) can protect against virus associated pathogenesis. Another example of immunosuppressed patients are HIV-infected patients. The method of the present invention can be used to serially monitor the level of disease immunity, such as e.g. anti-CMV immunity, in persons at risk of developing a respective disease, as loss of this immune function may be associated with development of the disease such as a CMV disease. Preferably, interferon gamma is determined as effector molecule in a respective test. The immune status of the transplant recipient can influence the (re)activation of CMV in transplant recipients. E. g. a robust interferon gamma response induced by a CMV specific antigen indicates a decreased risk of CMV disease, as the patient has a strong cell mediated response and thus protection from the virus. A minimal interferon gamma response indicates an increased risk of CMV disease, as either no or a very low cell-mediated immunity exists. Data show that patients with a positive CMV test remain free from CMV diseases significantly more often and for longer than patients with a negative test after cessation of anti-viral prophylaxis. Thus, patients who have a cellular immune response to CMV at the end of prophylaxis have a significantly lower risk of developing CMV disease than those who do not have a detectable immune response. Therefore, the method according to the present invention may predict a development of late onset CMV disease in transplant recipients and thus is very useful in patient management.

The subject may alternatively have or may be tested for a disease condition selected from Celiac's disease, autoimmune diabetes, alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic, inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arrthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis, vitiligo and inflammatory bowel disease.

The subject may alternatively have or may be tested for a cancer. Cancer therapy also is somewhat dependent on cell-mediated immunity and the cancer itself or drugs used to treat cancer can lead to immunosuppression. Cancers contemplated herein include: a group of diseases and disorders that are characterized by uncontrolled cellular growth (e.g. formation of tumor) without any differentiation of those cells into specialized and different cells. Such diseases and disorders include ABU protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary 'cancer, polycythemia vera, prostate cancer, rare-cancers-and-associated-disorders, renal cell carcinoma, retinoblastoma, rhabdomyosarcoma, Rothmund-Thomson syndrome, salivary' gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), tropho-blastic cancer, urethral cancer, urinary system cancer, uroplakins, uterine sarcoma, uterus cancer, vaginal cancer, vulva cancer, Waldenstrom's-macroglobulinemia and Wilms' tumor.

The subject may alternatively be exposed to or may be tested for exposure to a protein toxicant.

Autoimmune diseases contemplated herein for detection and/or monitoring include inter alia alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arrthritis, sarcoidosis, scleroderma, Sjogren's syndrome, stiff-man syndrome, systemic lupus erythematosus, Takayasu arteritis, temporal arteritis/gianT-cell arteritis, ulcerative colitis, uveitis, vasculitis and vitiligo.

Other disease conditions contemplated include inflammatory disease conditions as they can lead to immunosuppression. Examples of inflammatory disease conditions contemplated by the present disclosure include but are not limited to those diseases and disorders which result in a response of redness, swelling, pain, and a feeling of heat in certain areas that is meant to protect tissues affected by injury or disease. Inflammatory diseases which can be treated using the methods of the present disclosure include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy. In terms of non-human applications, the present disclosure extends to detecting EIPH in horses and various conditions in animals such as facial tumor disease in the Tasmanian Devil.

In the above aspects, the antigen may be derived from the pathogenic agent, be associated with the disease condition or cancer or be a toxicant. Alternatively, the infection, disease condition, cancer or toxicant may suppress cell-mediated immunity in which case any antigen to which the subject has been prior exposed could be employed.

Particularly advantageous embodiments described in the description and the claims of the method according to the first aspect are again described in the following. According to the first aspect, the present disclosure provides a method for measuring cell-mediated immune response activity, said method comprising
  (a) providing an incubation composition by contacting a sample comprising immune cells capable of producing immune effector molecules following stimulation by an antigen with at least one antigen and with at least one non-reducing sugar, and
  (b) detecting the presence or level of at least one immune effector molecule.

According to one embodiment, the non-reducing sugar is a non-reducing disaccharide, preferably being selected from trehalose and sucrose. The concentration of the non-reducing sugar in the incubation composition is according to one embodiment at least 1.5 mg/ml, preferably at least 2 mg/ml. Suitable ranges for the concentration of the non-reducing sugar in the incubation composition are also described above and it is referred to the above disclosure.

According to one embodiment, the non-reducing sugar is selected from trehalose, mannitol, sucrose and raffinose. As is demonstrated by the examples, these non-reducing sugars increase the response levels. Trehalose is particularly preferred because here, the largest increase in the response level was observed. Furthermore, the enhancing effect may be preserved during storage.

According to one embodiment, in step (a), the sample is contacted with a composition which comprises the antigen and the non-reducing sugar. According to one embodiment, wherein the sample is a whole blood sample, the composition additionally comprises an anticoagulant, preferably heparin. According to one embodiment, the composition comprising the antigen, the non-reducing sugar and optionally an anticoagulant is comprised in a sample collection vessel. As described herein, such sample collection vessel can e.g. be an evacuated blood collection vessel. According to one embodiment, the composition is a spray-dried composition. Suitable embodiments are described herein.

According to one embodiment, the sample has one or more of the following characteristics:
i) the sample was obtained from a human subject;
ii) the sample was obtained from a human subject that is immunosuppressed or immunodeficient
iii) the sample comprises immune cells selected from the group consisting of NK-cells, T-cells, B-cells, dendritic cells, macrophages and monocytes; and/or
iv) the sample is whole blood.

According to one embodiment, the antigen is selected from the group consisting of peptides, proteins, including glycoproteins, phosphoproteins and phospholipoproteins, carbohydrates, phospholipids and fragments of the foregoing and preferably is provided by one or more peptides.

According to one embodiment, two or more different antigens are used in step (a) and/or two or more different effector molecules are detected in step (b).

According to one embodiment, one or more peptides are used as antigen having a length selected from 5 to 100 amino acids or 7 to 50 amino acids. According to an advantageous embodiment, the antigen is provided by one or more peptides that are recognized by a CD8$^+$ cytotoxic T-cell. Preferably, in this embodiment, the antigen is provided by one or more peptides having a length of less than 15 amino acids, preferably having a length selected from 7-14 amino acids. Details of the respective peptides were described above and it is referred to the above disclosure.

According to one embodiment, the antigen is provided by at least two sets of peptides, a first set comprising at least one peptide of from 7 to 14 amino acid residues in length and a second set comprising at least one peptide of from 15 amino acid residues or greater which peptides encompass all or part of a protein antigen. Details of the respective peptide sets were described above and it is referred to the above disclosure.

According to an advantageous embodiment, the antigen is provided by one or more synthetic peptides. Details of the peptide(s) were described above and it is referred to the respective disclosure.

According to one embodiment, the sample is contacted with an antigen associated with or representative for a disease or condition for which the cell-mediated immune response is to be tested. According to an advantageous embodiment, the antigen is a disease specific antigen, in particular a pathogen specific antigen. For example, the antigen may be derived from and thus may be cross-reactive with an antigen from a pathogen associated with a disease condition or is a tumor-associated antigen associated with a cancer. As described above, the pathogen may be a bacterium, a virus, a parasite, yeast or a fungus. Non-limiting examples will be described in the following. For example, the bacterium may be selected from Gram positive and Gram negative microorganisms, in particular *Mycobacterium* species such as *Mycobacterium tuberculosis, Staphylococcus* species, *Streptococcus* species, *Escherichia coli, Salmonella* species, *Clostridium* species, *Shigella* species, *Proteus* species, *Bacillus* species, *Hemophilus* species and *Borrelia* species. The virus may be selected from Hepatitis virus such as Hepatitis B virus and Hepatitis C virus, Herpes virus, CMV virus and Human immune deficiency virus (HIV). The parasite may be selected from *Plasmodium* species, ringworm and liver parasites.

According to one embodiment, the antigen is from or is specific for a virus, preferably cytomegalovirus (CMV). Preferably, said antigen is provided by one or more peptides having a length of 7 to 14 amino acid residues, 7 to 13 amino acid residues or 8 to 12 amino acid residues. As described above, the one or more peptides may be synthetic peptides.

According to one embodiment, the immune effector molecule detected in step (b) has one or more of the following characteristics:
i) it is a cytokine;
ii) it is a chemokine;
iii) it is produced in response to cell activation, stimulation or re-stimulation by the antigen;
iv) it is selected from the group consisting of interferons, interleukins (IL), Tumor Necrosis Factor alpha (TNF-α), Transforming Growth Factor beta (TGF-β), a Colony Stimulating Factor (CSF) such as Granulocyte (G)-CSF or Granulocyte Macrophage (GM)-CSF, complement component 5a (C5a), Groα (CXCL1), sICAM-1 (CD54), IP-10 (CXCL10), 1-TAC (CXCL11), MCP-1 (CCL2), MIF (GIF), MIP-1α (CCL3), MIP-1β (CCL4), Serpin E1 (PAI-1), RANTES (CCL5) or MIG (CXCL9); and/or
v) the immune effector molecule is IFN-gamma.

According to one embodiment of the method, the presence or level of an immune effector molecule is determined based on the immune effector molecule or is determined based on the RNA expression level of the immune effector molecule. Suitable embodiments were described above.

According to one embodiment, the method according to any of the foregoing embodiments is for monitoring or determining the presence, absence, level or stage of a disease or condition selected from the group consisting of an infection by a pathogenic agent, an autoimmune disease, a cancer, an inflammatory condition, exposure to a toxic agent, response to a therapeutic agent, an immunodeficiency and an, immunosuppression. Preferably, the magnitude of the cell-mediated immune response correlates with the state, progression and/or severity of a disease condition. According to one embodiment, the method according to any of the foregoing embodiments is for detecting or monitoring a disease, an infection and/or the response to therapy, in particular immunotherapy or a therapy with immunosuppressive agents.

According to one embodiment, the method according to any of the foregoing embodiments comprises
(a) providing an incubation composition by contacting a whole blood sample obtained from a human subject with a composition comprising at least one peptide antigen and at least one non-reducing disaccharide, preferably trehalose or sucrose, and incubating the incubation composition for at least 2 hours; and
(b) measuring the presence or level of IFN-gamma released due to the stimulation with the antigen;
wherein the presence or quantity of detected IFN-gamma is indicative of the level of cell-mediated immune responsiveness of the human subject.

According to one embodiment, the method according to any of the foregoing embodiments comprises (c) comparing the determined immune effector molecule level or a value derived therefrom with a reference-level.

The present disclosure further provides a method of treatment of a subject having a pathogenic infection, an autoimmune disorder or cancer or a propensity for developing such a condition or disorder, the method comprising performing the method for measuring cell-mediated response activity according to the first aspect of the present invention wherein the determined presence or level of the immune effector molecule is indicative of the level of cell-mediated responsiveness of the subject which is indicative of the presence, absence, level or state of the condition or disorder and then treating the condition or disorder. Details of the method according to the first aspect were described above and it is referred to the above disclosure. Compositions, Kits and Uses, According to a second aspect the present invention provides a composition for inducing a cell mediated immune response in a sample, comprising a) at least one isolated antigen;
b) at least one non-reducing sugar;
c) optionally at least one anticoagulant.

Details regarding the composition, the composition form, suitable antigens, non-reducing sugars and anticoagulants were described above in conjunction with the method according to the present invention and it is referred to the above disclosure. Such composition can be used e.g. in the method according to the first aspect. Suitable applications, including uses/purposes, diseases and conditions that can be analysed using such a composition and accordingly; suitable uses of said composition were described in detail above and it is referred to the above disclosure. The composition according to the second aspect is particular suitable for use in the above described methods, applications and uses. According to one embodiment, the composition does not comprise a simple sugar. According to one embodiment, the composition does not comprise a reducing sugar. Preferably, the composition is a semi-liquid, gel-like or solid composition. Preferably, it is a dried composition. According to one embodiment, the composition is a spray-dried composition.

Non-limiting, advantageous embodiments are again described in the following:

The non-reducing sugar may have the characteristics as described above in conjunction with the method according to the first aspect and it is referred to the respective disclosure which also applies here. As described above, the non-reducing sugar is not used as stabilizer for the antigen but is used to increase the response level. As is shown in the examples, non-reducing sugars such as trehalose, mannitol, sucrose and raffinose increase the response, levels. According to one embodiment, the non-reducing sugar is a non-reducing disaccharide. The non-reducing disaccharide may be selected from trehalose and sucrose. The concentration of the non-reducing sugar in the composition according to the second aspect is according to one embodiment such that when said composition is contacted with the intended amount of sample, the resulting incubation composition comprises the non-reducing sugar in a concentration of at least 1.5 mg/ml, preferably at least 2 mg/ml. Suitable ranges for the concentration of the non-reducing sugar in the incubation composition are also described above in conjunction with the method according to the first aspect and it is referred to the above disclosure. Suitable and preferred sample materials were also described above in conjunction with the method according to the first aspect and it is referred to the above disclosure. According to one embodiment, the sample has one or more of the following characteristics:

i) the sample was obtained from a human subject;
ii) the sample was obtained from a human subject that is immunosuppressed or immunodeficient
iii) the sample comprises immune cells selected from the group consisting of NK-cells, T-cells, B-cells, dendritic cells, macrophages and monocytes; and/or
iv) the sample is whole blood.

According to one embodiment, the antigen comprised in the composition is selected from the group consisting of peptides, proteins, including glycoproteins, phosphoproteins and phospholipoproteins, carbohydrates, phospholipids and fragments of the foregoing and preferably is provided by one or more peptides.

According to one embodiment, the composition comprises two or more different antigens.

According to one embodiment, the composition comprises one or more peptides as antigen, wherein the one or more peptides have a length selected from 5 to 100 amino acids or 7 to 50 amino acids. According to an advantageous embodiment, the composition comprises as antigen one or more peptides that are recognized by a CD8$^+$ cytotoxic T-cell. Preferably, in this embodiment, the antigen is provided by one or more peptides having a length of less than 15 amino acids, preferably having a length selected from 7-14 amino acids. Details of the respective peptides were described above in conjunction with the method according to the first aspect and it is referred to the above disclosure.

According to one embodiment, the composition comprises an antigen that is provided by at least two sets of peptides, a first set comprising at least one peptide of from about 7 to 14 amino acid residues in length and a second set comprising at least one peptide of from 15 amino acid residues or greater which peptides encompass all or part of a protein antigen. Details of the respective peptide sets were described above in conjunction with the method according to the first aspect and it is referred to the above disclosure.

According to an advantageous embodiment, the composition comprises an antigen that is provided by one or more synthetic peptides. Details of the peptide(s) were described above and it is referred to the respective disclosure.

According to one embodiment, the composition comprises an antigen associated with or representative for a disease or condition for which the cell-mediated immune response is to be tested.

According to an advantageous embodiment, the antigen comprised in the composition is a disease specific antigen, in particular a pathogen specific antigen. For example, the antigen may be derived from and thus may be cross-reactive with an antigen from a pathogen associated with a disease condition or is a tumor-associated antigen associated with a cancer. As described above, the pathogen may be a bacterium, a virus, a parasite, yeast or a fungus. Non-limiting examples will be described in the following. For example, the bacterium may be selected from Gram positive and Gram negative microorganisms, in particular *Mycobacterium* species such as *Mycobacterium tuberculosis, Staphylococcus* species, *Streptococcus* species, *Escherichia coli, Salmonella* species, *Clostridium* species, *Shigella* species, *Proteus* species, *Bacillus* species, *Hemophilus* species and *Borrelia* species. The virus may be selected from Hepatitis virus such as Hepatitis B virus and Hepatitis C virus, Herpes virus, CMV virus and Human immune deficiency virus (HIV). The parasite may be selected from *Plasmodium* species, ringworm and liver parasites.

According to one embodiment, the composition comprises an antigen that is from or is specific for a virus, such as cytomegalovirus (CMV). Preferably, said antigen is provided by one or more peptides having a length of 7 to 14 amino acid residues, 7 to 13 amino acid residues or 8 to 12 amino acid residues. As described above, the one or more peptides may be synthetic peptides.

The composition can be comprised in a sample collection vessel, suitable and advantageous embodiments of such vessel such as an evacuated blood collection vessel, are described herein and it is referred to the respective disclosure.

Also provided by the present invention is an incubation composition, comprising at least one isolated antigen, at least one non-reducing sugar, immune cells capable of producing immune effector molecules following stimulation by an antigen, preferably T lymphocytes, and optionally at least one anticoagulant. Preferably, the incubation composition was prepared from and thus comprises a whole blood sample. According to one embodiment, the incubation composition was prepared by contacting a composition according to the second aspect with a sample. Suitable and preferred sample materials were described above in conjunction with the method according to the first aspect and it is referred to the above disclosure. According to one embodiment, the sample has one or more of the following characteristics:

i) the sample was obtained from a human subject;
ii) the sample was obtained from a human subject that is immunosuppressed or immunodeficient
iii) the sample comprises immune cells selected from the group consisting of NK-cells, T-cells, B-cells, dendritic cells, macrophages and monocytes; and/or
iv) the sample is whole blood.

Preferably, the incubation composition is obtained by contacting a composition according to the second aspect of the present invention with a whole blood sample obtained from a subject, preferably obtained from a human. Details regarding the composition according to the second aspect, the incubation composition, its preparation, suitable antigens, non-reducing sugars and anticoagulants were described above in conjunction with the method according to the present invention and the composition according to the second aspect and it is referred to the above disclosure. The anticoagulant is preferably heparin. According to one embodiment, the incubation composition comprises the non-reducing sugar in a concentration of at least 1.5 mg/ml, preferably at least 2 mg/ml. Suitable ranges for the concentration of the non-reducing sugar in the incubation composition are also described above in conjunction with the method according to the first aspect and it is referred to the above disclosure. According to one embodiment, the non-reducing sugar is selected from trehalose, mannitol, sucrose and raffinose. As described above, according to an advantageous embodiment, the non-reducing sugar is a non-reducing disaccharide, preferably being selected from trehalose and sucrose.

Also provided is a sample collection vessel, in particular a sample collection tube, comprising a respective composition comprising
a) at least one isolated antigen;
b) at least one non-reducing sugar;
c) optionally at least one anticoagulant.

The composition comprised in the sample collection vessel is preferably the composition according to the second aspect. Details regarding the composition, suitable antigens, non-reducing sugars and anticoagulants were described above and it is referred to the above disclosure. Such sample collection vessel can be used e.g. in the method according to the first aspect. Suitable applications, including uses/purposes, diseases and conditions that can be analysed using such a sample collection vessel were described in detail above and it is referred to the above disclosure. The sample collection vessel according to the third aspect is in particular suitable for use in the above described methods, applications and uses. Preferably, the composition is sprayed onto the inside of the vessel which preferably is an evacuated blood collecting tube. By using such ready-to-use collection vessels in the method of the present invention, the conditions of the method are optimized and standardized and the handling is simplified.

The method according to the invention is preferably performed using a kit which provides the materials necessary for executing the method steps. Such a kit preferably comprises standardized material which ensures that the method is performed under optimized conditions, thereby ensuring that the results obtained from different samples or patients or by different practitioners are comparable to each other. Therefore, in a fourth aspect, the present disclosure also provides a kit for measuring cell-mediated immune response activity in a subject, comprising at least one antigen, at least one non-reducing sugar, at least one sample collection vessel and at least one detection means for detecting at least one immune effector molecule. Preferably, the antigen and the non-reducing sugar are provided in form of a single composition. For this purpose, the composition according to the second aspect of the invention can be used and it is referred to the above disclosure for details of said composition. Details regarding the composition, the antigen and the non-reducing sugar were also described above in conjunction with the method and the composition according to the present invention and it is referred to the above disclosure. According to one embodiment, the kit comprises a sample collection vessel such as a blood collection tube which comprises the composition comprising the antigen and the non-reducing sugar. Preferably, the composition additionally comprises an anti-coagulant such as heparin. As described, the composition comprised in the sample collection container can be the composition according to the second aspect. Preferably, the detection means is an immunodetection reagent such as a labeled antibody. However, for assays that are based on the detection of the mRNA expression level, the detection means can be provided by primers and/or probes specific for the immune effector molecule to be detected. Suitable assays and detection means are known to the skilled person and were also described above.

According to a further aspect, the present invention pertains to the use of a non-reducing sugar in an immunological assay for measuring cell-mediated response activity, wherein the addition of the non-reducing sugar during incubation of the sample with the antigen increases the release of an immune effector molecule from immune cells that respond to the antigen tested in said assay.

Details regarding the non-reducing sugar, preferred concentrations, the immunological assay and applications thereof in the medical field, suitable and preferred antigens, immune effector molecules and immune cells were described above in conjunction with the method according to the present invention and it is referred to the above disclosure. The non-reducing sugar may have one or more of the following characteristics:
 i) the non-reducing sugar is a disaccharide;
 ii) the non-reducing sugar is selected from trehalose and sucrose;
 iii) the non-reducing sugar is used in a concentration of at least 1 mg/ml, preferably 2 mg/ml in the incubation composition comprising the sample to be tested and the antigen; and/or
 iv) the non-reducing sugar is provided in the form of a composition which additionally comprises the antigen to be tested and optionally an anticoagulant.

According to one embodiment, the non-reducing sugar is selected from trehalose, mannitol, sucrose and raffinose.

The use of a non-reducing sugar as described herein, e.g. trehalose, in an assay to determine or monitor cell-mediated immunity has significant advantages. As described above, preferably the non-reducing sugar is provided together with the antigen in form of a single composition which is contacted with the sample. According to one embodiment, no reducing sugar is added for incubation and/or is comprised in the composition comprising the non-reducing sugar and the antigen. As described above, the non-reducing sugar is not used as stabilizer for the antigen. According to an advantageous embodiment, the antigen is provided by one or more peptides, preferably synthetic peptides, that are recognized by a $CD8^+$ cytotoxic T-cell. Preferably, in this embodiment, the antigen is provided by one or more peptides, preferably synthetic peptides, having a length of less than 15 amino acids, preferably having a length selected from 7-14 amino acids.

According to a further aspect, the present disclosure pertains to the use of the composition according to second aspect of the invention, a sample collection vessel according to the third aspect of the invention and/or a kit according to the fourth aspect of the invention in an assay for measuring cell-mediated response activity. Details regarding suitable and preferred uses and applications were described above and it is referred to the above disclosure. According to one embodiment, the assay is for monitoring or determining the presence, absence, level or stage of a disease or condition selected from the group consisting of an infection by a pathogenic agent, an autoimmune disease, a cancer, an inflammatory condition, exposure to a toxic agent, response to a therapeutic agent, an immunodeficiency and an immunosuppression. According to one embodiment, the assay is for detecting or monitoring a disease, an infection and/or the response to therapy, in particular immunotherapy or a therapy with immunosuppressive agents. According to one embodiment, the composition according to second aspect of the invention, a sample collection vessel according to the third, aspect of the invention and/or a kit according to the fourth aspect of the invention is used in the method according to the first aspect which is described in detail above and in the claims.

This invention is not limited by the exemplary methods and materials disclosed herein. Numeric ranges described herein are inclusive of the numbers defining the range. The headings provided herein are not limitations of the various aspects or embodiments of this invention which can be read by reference to the specification as a whole. According to one embodiment, subject-matter described herein as comprising certain steps in the case of methods or as comprising certain ingredients in the case of e.g. compositions, solutions and/or mixtures refers to subject-matter consisting of the respective steps or ingredients. It is preferred to select and combine preferred embodiments described herein and the specific subject-matter arising from a respective combination of preferred embodiments also belongs to the present disclosure.

The invention will now be illustrated in further detail by the following non-limiting examples.

EXAMPLES

Example 1: Effects of Trehalose on the Sensitivity of the Epstein-Barr Virus Assay Investigations using QuantiFERON technology to measure responses to the model antigen EBNA-1 from the Epstein-Barr virus were performed to assess increases in assay sensitivity induced by the addition of non-reducing sugars to the incubation mixture. Briefly, EBNA-1 peptides were added to a blood collection tube, plus/minus 3 concentrations of a trehalose solution (0.5, 1.0 or 2.0 mg/ml trehalose). QuantiFERON assay measuring anti-EBV cellular immune responses was run according to the manufacturer's instructions. The IFN-gamma response was determined and compared depending on the concentration of trehalose. An increase in IFN-gamma response was observed with increasing trehalose concentration. A concentration of 2 mg/ml trehalose provided the best results in this test assay.

These studies demonstrate that the addition of a non-reducing sugar, such as trehalose, to the whole blood assay results in a significant increase in the IFN-gamma response in a cell mediated immune response assay. Due to the increase in IFN-gamma response that is induced by the addition of the non-reducing sugar, the sensitivity of the assay is enhanced.

Example 2: Storage Stability of a Prior Art Assay

In this example, a cell-mediated immune response test against CMV was performed and the storage stability of assay components was analysed. As antigen, synthetic peptides, 8-12 amino acids in length, from cytomegalovirus-associated antigens were used. The CMV-associated synthetic peptides were formulated in solution containing a simple sugar (glucose) and sprayed onto the inside of a blood collection tube and dried. Therefore, the antigen and the simple sugar were comprised in one composition. Stability testing of said composition comprised in the blood collection tube indicated that assay activity diminished with time stored at room temperature. Moreover, assay activity of the CMV device was lost when the blood collection device comprising the spray-dried composition comprising the antigen and glucose was stored at 55° C. for a period greater than 3 weeks (21 days). Therefore, respective compositions and accordingly, collection tubes comprising respective compositions were unsuitable for use as ready-to-use kit components due to the lacking storage stability. Removal of glucose from the composition restored the stability and function of the assay. Therefore, it was not feasible to include the simple sugar together with the antigen in a composition. Instead, for increasing the assay sensitivity the simple sugar had to be added separately to the sample during preparation of the incubation composition.

In contrast, compositions comprising the antigen and a non-reducing sugar as taught herein may maintain the increased assay sensitivity also over prolonged storage periods.

These results were also confirmed by further experiments. CMV tubes containing either glucose or no glucose were stored for three weeks at 4° C., 22° C., 37° C. and 55° C. and were then tested with blood samples from 4 reactive donors and 1 non-reactive donor. Table 1 shows the average results obtained with the reactive donors. At the indicated temperatures, the CMV tubes containing glucose are less reactive then either the tubes stored at 4° C. or 22° C. and show a marked decrease in responses relative to the liquid formulation (reference standard) used to prepare the CMV tubes. In contrast, tubes lacking glucose did not show a respective loss in reactivity.

TABLE 1

Effect of glucose during storage. Shown is the fold difference to retention (average IU/ml)

|  | 55° C. | 37° C. | 22° C. | 4° C. |
| --- | --- | --- | --- | --- |
| CMV tubes with glucose | 0.58 | 0.75 | 1.48 | 1.34 |
| CMV tubes without glucose | 0.97 | 0.91 | 1.01 | 1.21 |

Example 3: Effect of the Addition of Trehalose on the IFN-Gamma Response in a QFN-CMV Tube QuantiFERON (QFN) CMV is a CE registered assay monitoring T cell immune memory directed against antigens derived from the Cytomegalovirus. The QFN-CMV blood tubes contain peptides designed to specifically activate CD8+ T cells to produce interferon gamma (IFN-gamma). These tubes only contain peptide and heparin, with no addition of any sugar molecule.

This experiment aimed to investigate the effect on the IFN-gamma response when the non-reducing sugar, trehalose, was added to QFN-CMV tubes. 0, 1, 5 or 10 mg/ml of a trehalose (in water) solution was added to QFN-CMV blood collection tubes. 1 ml of blood from 17 healthy donors with a known anti-CMV T cell response was then added to each of the four tubes, and in addition a Nil tube and a Mitogen tube were run as controls. The QFN assay was then run according to the package insert. All values had the Nil value subtracted. IFN-gamma levels in IU/ml were normalized against the respective QFN-CMV+0 mg/ml trehalose (untreated control) to generate a 'fold-change' unit; to control for inter-donor variation in response magnitude. Healthy donors without a detectable anti-CMV immune response were included to control against non-specific IFN-gamma induction by trehalose.

The addition of trehalose resulted in a concentration-dependent increase in the mean level of IFN-gamma (expressed as fold change IFN-gamma versus the matched untreated control). A significant increase in the effect was observed with the addition of 5 and 10 mg/ml trehalose; Friedmans test with Dunns multiple comparisons test. The results are shown in FIG. 1. No significant increase in the background level of IFN-gamma in the CMV-negative control donors was observed (data not shown).

The addition of trehalose to a QFN assay significantly increases the level of IFN-gamma produced in response to the specific antigen(s) contained with the blood collection tube without non-specifically increasing the background IFN-gamma level.

Example 4: Effect of the Addition of Trehalose on the IFN-Gamma Response in a QFN-TB Tube To confirm the observation that the addition of the non-reducing sugar trehalose to an assay assessing peptide-specific cellular immunity such as the QuantiFERON (QFN) assay enhances the quantitative result of the test, QFN tubes were manufactured with the addition of a non-reducing sugar. QFN blood collection tubes were manufactured to contain synthetic peptides from the *Mycobacterium tuberculosis* (MTB) antigens ESAT-6 and CFP-10 either without the addition of any sugar or with the addition of the non-reducing sugar trehalose.

Figure 2:
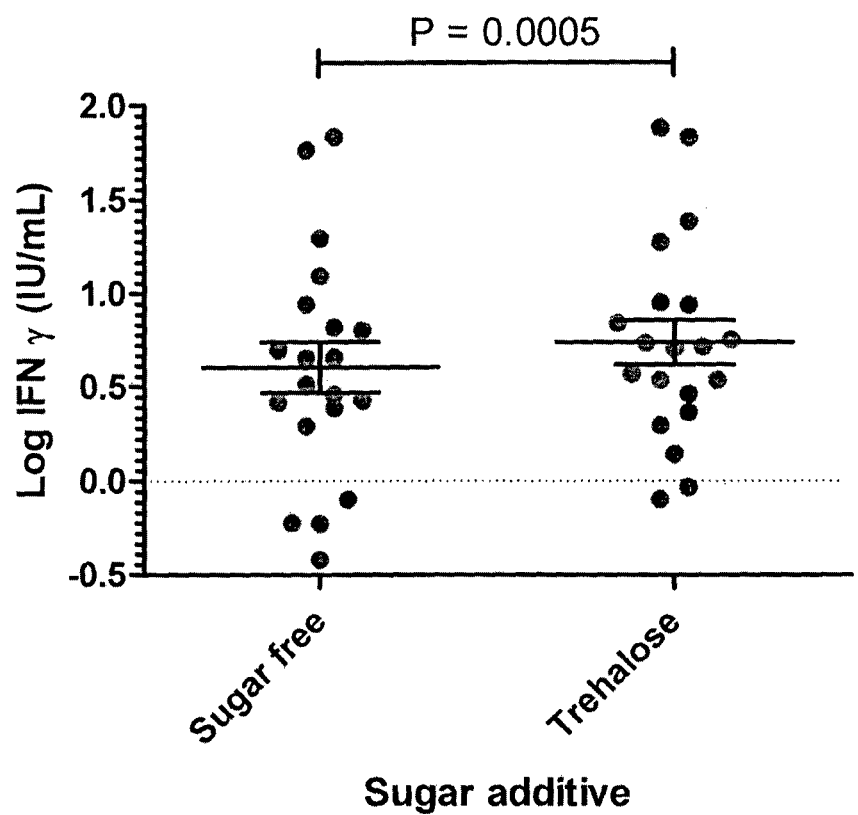
FIG. 2: Effect of trehalose addition on IFN-gamma response in a QFN-TB assay.

Whole blood from 20 subjects with evidence of MTB infection, confirmed using the QuantiFERON Gold In Tube assay, was tested using the established QuantiFERON platform technology, however, employing the modified QFN TB antigen tubes described above which were either manufactured without (sugar free) or with a non-reducing sugar (Trehalose). The assay was run in accordance with the QFT Gold package insert which is an established assay. In this paired clinical analysis, the inclusion of the non-reducing sugar, trehalose, in the TB antigen tube significantly enhanced the quantitative response of the assay (P=0.0005) as is shown in FIG. 2. Values from the tubes (y-axis) are shown as Log transformed IFN-gamma IU/ml values (with the nil tube values subtracted). A paired one-tailed t test was performed to show statistical significance between the two cohorts. The results clearly demonstrate that the addition of trehalose increases the interferon gamma response as was shown in subjects with TB infection.

Figure 3:
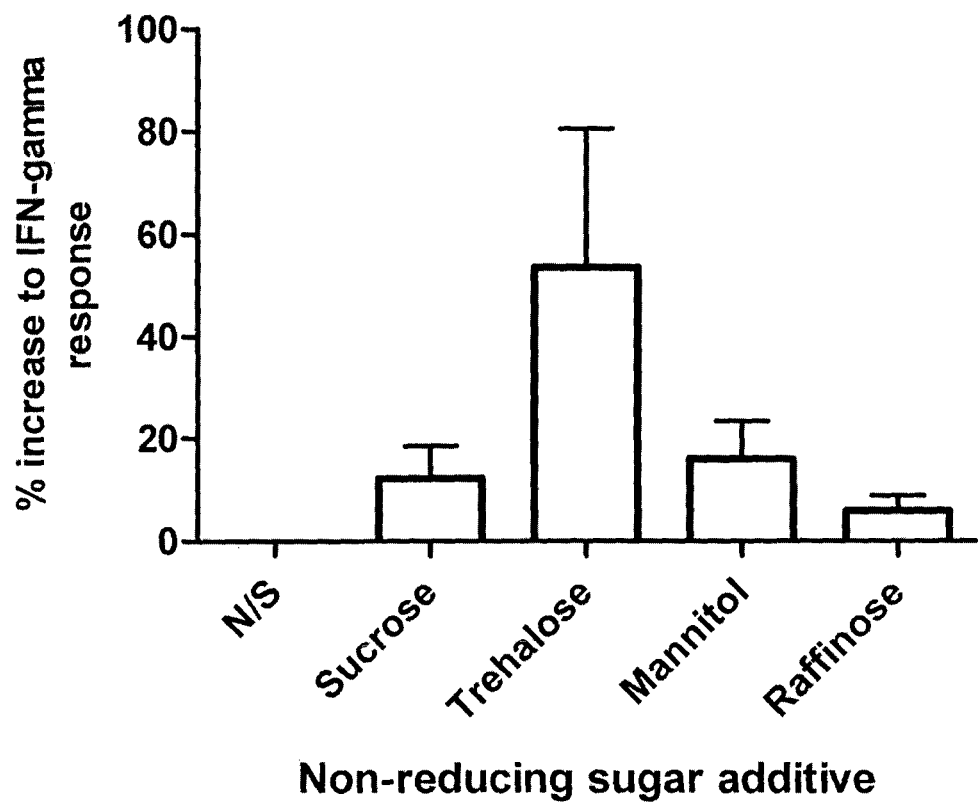
FIG. 3: Four different non-reducing sugars augment the quantitative QFN CMV result.

Example 5: Addition of Different Non-Reducing Sugars Increases the Quantitative INF-Gamma Response The observed enhancement effect was also demonstrated with additional non-reducing sugars. For this experiment, four different non-reducing sugars were added to QFN CMV antigen tubes and a corresponding Nil tube. To reach a final blood concentration of 2 mg/ml, a corresponding solution of sucrose, trehalose, mannitol and raffinose in PBS was added to whole blood obtained from 5 donors. Hence, a QFN assay was performed on blood from 5 donors, using QFN CMV tubes either without (N/S) or with the addition of a non-reducing sugar (sucrose, trehalose, mannitol or raffinose). The assay was run in accordance with the QFN package insert which is an established assay. The results are shown in FIG. 3. The x-axis (see FIG. 3) indicates the tested conditions. The background (value from Nil tubes with/without the addition of the respective sugar) was subtracted from the corresponding CMV tube and the percentage increase in the IFN-gamma value (IU/ml) over the non-additive tube calculated (y axis). The results demonstrate that an increased response to the CMV antigens as measured by the quantitative IFN-gamma (IU/ml) value was observed with all four non-reducing sugars. Thus, all tested non-reducing sugars had a beneficial effect on the INF-gamma response. With trehalose the highest increase was seen, followed by mannitol, sucrose and raffinose.

The invention claimed is:
1. A method of increasing sensitivity in an assay for measuring cell-mediated immune response activity in a sample, comprising:
(a) incubating in a container an incubation composition that is obtained by contacting
(i) a sample obtained from a subject, said sample comprising immune cells which comprise T-cells, the T-cells being capable of responding to an antigen to which said T-cells have previously been exposed by producing immune effector molecules that include interferon-gamma (IFN-γ) following re-stimulation by the antigen,
(ii) at least one antigen that comprises a pathogen specific antigen from a pathogenic or infectious agent to which the immune cells have previously been exposed or a pathogen specific antigen that is cross-reactive with an antigen from a pathogenic or infectious agent to which the immune cells have previously been exposed, and
(iii) at least one non-reducing disaccharide that is capable of stimulating increased IFN-γ production by the T-cells in response to the antigen compared to IFN-γ production by the T-cells when the non-reducing disaccharide is not present, under conditions and for a time sufficient to allow stimulation of the immune cells by the antigen and production of the immune effector molecules that include IFN-γ; and
(b) detecting a presence or level of at least one immune effector molecule in the incubation composition, wherein said detecting the presence or level of said at least one immune effector molecule comprises detecting the presence or level of IFN-γ and wherein antigen-stimulated IFN-γ production by the T-cells in the incubation composition when the non-reducing disaccharide is present is increased compared to IFN-γ production when the non-reducing disaccharide is not present, and thereby increasing sensitivity in the assay for measuring cell-mediated immune response activity in the sample,
wherein the at least one immune effector molecule is selected from the group consisting of IFN-γ, IL-2, IL-4, IL-6, IL-8, IL-10, IL-12, IL-13, IL-16, IL-17, IL-1α, IL-1β, IL-1rα, TNF-α, TGF-β, (G)-CSF, (GM)-CSF, complement component 5a, Groα (CXCL1), sICAM-1, IP-10 (CXCL10), I-TAC (CXCL11), MCP-1 (CCL2), MIF (GIF), MIP-1α (CCL4), Serpin E1, RANTES, and MIG (CCL5),
and wherein at least one of (i)-(v) is true:
(i) the antigen comprises one or more peptides from a protein of the pathogenic or infectious agent to which the immune cells have previously been exposed or from a protein that is cross-reactive with the pathogenic or infectious agent to which the immune cells have previously been exposed, wherein the one or more peptides have a length selected from (a) 5 to 100 amino acids and (b) 7 to 50 amino acids;
(ii) the antigen comprises one or more synthetic peptides that are cross-reactive with the antigen of (i) and that have a length selected from (a) 5 to 100 amino acids and (b) 7 to 50 amino acids;
(iii) the antigen comprises at least two sets of peptides that comprise all or part of a protein antigen from a protein of the pathogenic or infectious agent to which the immune cells have previously been exposed or from a protein that is cross-reactive with the pathogenic or infectious agent to which the immune cells have previously been exposed, a first set comprising at least one peptide of the protein antigen of from about 7 to 14 amino acid residues in length and a second set comprising at least one peptide of the protein antigen of at least 15 amino acid residues, wherein the peptides comprise amino acids that span all or part of the protein antigen;
(iv) the antigen comprises one or more peptides of (i)-(iii) that are recognized by a CD8+ cytotoxic T-cell; and
(v) the antigen comprises one or more peptides that are recognized by a CD8+ cytotoxic T-cell and the one or more peptides (1) are from a protein of the pathogenic or infectious agent to which the immune cells have previously been exposed or from a protein that is cross-reactive with the pathogenic or infectious agent to which the immune cells have previously been exposed, and (2) have a length of less than 15 amino acids or have a length selected from 7-14 amino acids.

2. The method of claim 1, wherein the non-reducing disaccharide is trehalose or sucrose.

3. The method of claim 1, wherein the non-reducing disaccharide has a concentration in the incubation composition of at least 1.5 mg/ml or at least 2 mg/ml.

4. The method of claim 1, wherein either:
(i) in step (a) the antigen and the non-reducing disaccharide are contacted with one another prior to being contacted with the sample, or
(ii) in step (a) the antigen and the non-reducing disaccharide are present in a sample collection vessel prior to being contacted with the sample in the sample collection vessel.

5. The method of claim 4, wherein the composition which comprises the antigen and the non-reducing disaccharide further comprises an anticoagulant and wherein the sample is a whole blood sample.

6. The method of claim 1, wherein the sample is selected from:
i) a sample that is obtained from a human subject;
ii) a sample that is obtained from a human subject that is immunosuppressed or immunodeficient;
iii) a sample that comprises immune cells selected from the group consisting of NK-cells, T-cells, B-cells, dendritic cells, macrophages and monocytes; and
iv) a sample that is whole blood.

7. The method of claim 1, wherein one of:
(i) step (a) comprises contacting the sample with at least two different antigens,
(ii) step (b) comprises detecting at least two different immune effector molecules, and
(iii) step (a) comprises contacting the sample with at least two different antigens and step (b) comprises detecting at least two different immune effector molecules.

8. The method of claim 1, wherein the pathogen specific antigen or the antigen that is cross-reactive with an antigen from a pathogenic or infectious agent is a disease specific antigen.

9. The method of claim 1, which is selected from the method in which:
i) the pathogen specific antigen is from a pathogen that is a bacterium, a virus, a parasite, yeast or a fungus;
ii) the pathogen specific antigen is a bacterium specific antigen wherein the bacterium is selected from a Gram positive microorganism, a Gram negative microorganism, a *Mycobacterium* species, *Mycobacterium tuberculosis*, a *Staphylococcus* species, a *Streptococcus* species, *Escherichia coli*, a *Salmonella* species, a *Clostridium* species, a *Shigella* species, a *Proteus* species, a *Bacillus* species, a *Hemophilus* species and a *Borrelia* species;
iii) the pathogen specific antigen is a virus specific antigen wherein the virus is selected from a Hepatitis virus, Hepatitis B virus, Hepatitis C virus, Herpes virus, CMV virus and Human immune deficiency virus (HIV);
iv) the pathogen specific antigen is from or is specific for a virus, and is provided by one or more peptides capable of being recognized by a CD8+ cytotoxic T_cell and having a length of 7 to 14 amino acid residues, 7 to 13 amino acid residues or 8 to 12 amino acid residues; and v) the pathogen specific antigen is from or is specific for a cytomegalovirus (CMV), and is provided by one or more peptides capable of being recognized by a CD8+ cytotoxic T-cell and having a length of 7 to 14 amino acid residues, 7 to 13 amino acid residues or 8 to 12 amino acid residues.

10. The method of claim 1, wherein increased sensitivity when the non-reducing disaccharide is present in the assay for measuring cell-mediated immune response activity in the sample, compared to the sensitivity when the non-reducing disaccharide is not present, permits determining that the immune cells comprising T-cells in the sample obtained from the subject have been previously exposed to the pathogenic or infectious agent comprising the pathogen specific antigen or to the pathogenic or infectious agent that comprises the antigen that is cross-reactive therewith.

11. The method of claim 1, wherein:

(a) the sample comprises a whole blood sample from a human subject;

(b) the step of incubating the incubation composition which comprises said sample, said at least one antigen, and said at least one non-reducing disaccharide, is for at least 2 hours; and (c) detecting comprises measuring in the incubation composition the presence or level of IFN-gamma released by the T-cells present in said immune cells due to re-stimulation with the antigen;

wherein the presence or level of detected IFN-gamma is indicative of a level in the sample of cell-mediated immune response activity against the pathogenic or infectious agent to which the immune cells have previously been exposed, and thereby increasing sensitivity in the assay for measuring cell-mediated immune response activity in the whole blood sample from the human subject.

12. The method of claim 1, wherein
the non-reducing sugar is trehalose.

13. The method of claim 5, wherein the anticoagulant is heparin.

14. The method of claim 11, wherein the non-reducing disaccharide is selected from trehalose and sucrose.

* * * * *